United States Patent
Beckham et al.

(10) Patent No.: US 10,335,155 B2
(45) Date of Patent: Jul. 2, 2019

(54) POSITIONING AND DETACHING IMPLANTS

(71) Applicant: Covidien LP, Mansfield, MA (US)

(72) Inventors: David Scott Beckham, Costa Mesa, CA (US); Christopher Charles Andrews, Lake Elsinore, CA (US)

(73) Assignee: Covidien LP, Mansfield, MA (US)

( * ) Notice: Subject to any disclaimer, the term of this patent is extended or adjusted under 35 U.S.C. 154(b) by 369 days.

(21) Appl. No.: 15/407,361

(22) Filed: Jan. 17, 2017

(65) Prior Publication Data
US 2017/0135701 A1    May 18, 2017

Related U.S. Application Data

(62) Division of application No. 13/308,476, filed on Nov. 30, 2011, now Pat. No. 9,579,104.

(51) Int. Cl.
*A61B 17/00* (2006.01)
*A61B 17/12* (2006.01)

(52) U.S. Cl.
CPC .... *A61B 17/12113* (2013.01); *A61B 17/1214* (2013.01); *A61B 17/12136* (2013.01); *A61B 17/12154* (2013.01); *A61B 17/12168* (2013.01); *A61B 2017/00526* (2013.01); *A61B 2017/12054* (2013.01); *Y10T 29/49925* (2015.01); *Y10T 29/49934* (2015.01); *Y10T 156/10* (2015.01)

(58) Field of Classification Search
CPC ........ A61B 17/12113; A61B 17/12154; A61B 2017/00526; A61B 2017/12054; A61B 2017/12081
See application file for complete search history.

(56) References Cited

U.S. PATENT DOCUMENTS

| | | | |
|---|---|---|---|
| 2,456,640 A | * | 12/1948 | Linde ............... H01B 17/26 174/152 R |
| 3,308,476 A | * | 3/1967 | Kleesattel ............. G01L 1/10 73/573 |
| 3,334,629 A | | 8/1967 | Cohn et al. |
| 3,834,394 A | | 9/1974 | Sessions et al. |
| 4,085,757 A | | 4/1978 | Pevsner |
| 4,282,875 A | | 8/1981 | Serbinenko et al. |
| 4,311,146 A | | 1/1982 | Wonder et al. |
| 4,327,734 A | | 5/1982 | White et al. |
| 4,341,218 A | | 7/1982 | Ue |

(Continued)

FOREIGN PATENT DOCUMENTS

CN    2456640    10/2001
CN    1652726    8/2005
(Continued)

*Primary Examiner* — Wade Miles
(74) *Attorney, Agent, or Firm* — Fortem IP LLP; Matthew Lincicum

(57) ABSTRACT

Intravascular implant systems and methods of positioning and detaching implants are described. One such system carries an implant by retaining an engagement member in a position proximal to an aperture at a distal end of the delivery system. The engagement member is retained proximal to the aperture by an elongate member that is coupled to the implant. Once the implant is in a desired implant position, the elongate member is released from the engagement member, and the implant is allowed to move away from the delivery system.

14 Claims, 10 Drawing Sheets

(56) References Cited

U.S. PATENT DOCUMENTS

| | | |
|---|---|---|
| 4,346,712 A | 8/1982 | Handa et al. |
| 4,364,392 A | 12/1982 | Strother et al. |
| 4,402,319 A | 9/1983 | Handa et al. |
| 4,441,495 A | 4/1984 | Hicswa |
| 4,494,531 A | 1/1985 | Gianturco |
| 4,517,979 A | 5/1985 | Pecenka |
| 4,545,367 A | 10/1985 | Tucci |
| 4,638,803 A | 1/1987 | Rand |
| 4,735,201 A | 4/1988 | O'Reilly et al. |
| 4,781,177 A | 11/1988 | Lebigot |
| 4,787,899 A | 11/1988 | Lazarus |
| 4,819,637 A | 4/1989 | Bell et al. |
| 4,832,055 A | 5/1989 | Palestrant |
| 4,944,746 A | 7/1990 | Iwata et al. |
| 4,957,501 A | 9/1990 | Lahille et al. |
| 4,990,155 A | 2/1991 | Wilkoff et al. |
| 4,994,069 A | 2/1991 | Ritchart et al. |
| 5,002,556 A | 3/1991 | Ishida et al. |
| 5,026,377 A | 6/1991 | Burton et al. |
| 5,035,706 A | 7/1991 | Giantureo et al. |
| 5,037,427 A | 8/1991 | Nobuyoshi et al. |
| 5,056,761 A | 10/1991 | Meglino et al. |
| 5,062,829 A | 11/1991 | Pryor et al. |
| 5,104,399 A | 4/1992 | Lazarus |
| 5,108,407 A | 4/1992 | Geremia et al. |
| 5,109,867 A | 5/1992 | Twyford et al. |
| 5,122,136 A | 6/1992 | Guglielmi et al. |
| 5,133,731 A | 7/1992 | Butler et al. |
| 5,133,732 A | 7/1992 | Wiktor |
| 5,147,370 A | 9/1992 | McNamara et al. |
| 5,167,624 A | 12/1992 | Butler et al. |
| 5,181,921 A | 1/1993 | Machida et al. |
| 5,192,301 A | 3/1993 | Satoh et al. |
| 5,211,658 A | 5/1993 | Clouse |
| 5,217,484 A | 6/1993 | Marks |
| 5,222,970 A | 6/1993 | Reeves |
| 5,224,953 A | 7/1993 | Morgentaler |
| 5,226,911 A | 7/1993 | Chee et al. |
| 5,234,437 A | 8/1993 | Sepetka et al. |
| 5,250,071 A | 10/1993 | Palermo |
| 5,256,146 A | 10/1993 | Ensminger et al. |
| 5,261,916 A | 11/1993 | Engelson |
| 5,263,964 A | 11/1993 | Purdy |
| 5,282,259 A | 1/1994 | Grois et al. |
| 5,282,806 A | 2/1994 | Haber et al. |
| 5,304,194 A | 4/1994 | Chee et al. |
| 5,304,195 A | 4/1994 | Twyford et al. |
| 5,312,415 A | 5/1994 | Palermo |
| 5,314,472 A | 5/1994 | Fontaine |
| 5,334,210 A | 8/1994 | Gianturco |
| 5,350,397 A | 9/1994 | Palermo et al. |
| 5,354,295 A | 10/1994 | Guglielmi et al. |
| 5,368,592 A | 11/1994 | Stern et al. |
| 5,382,259 A * | 1/1995 | Phelps ............ A61B 17/12022 604/907 |
| 5,382,260 A | 1/1995 | Berlo et al. |
| 5,382,261 A | 1/1995 | Palmaz et al. |
| 5,397,345 A | 3/1995 | Lazarus |
| 5,417,708 A | 5/1995 | Hall et al. |
| 5,423,829 A | 6/1995 | Pham et al. |
| 5,423,849 A | 6/1995 | Samson et al. |
| 5,443,454 A | 8/1995 | Tanabe et al. |
| 5,443,478 A | 8/1995 | Purdy |
| 5,456,693 A | 10/1995 | Dapper et al. |
| 5,476,472 A | 12/1995 | Paul et al. |
| 5,480,382 A | 1/1996 | Hammerslag et al. |
| 5,490,859 A | 2/1996 | Mische et al. |
| 5,498,227 A | 3/1996 | Mawad et al. |
| 5,499,985 A | 3/1996 | Utley et al. |
| 5,507,769 A | 4/1996 | Marin et al. |
| 5,522,822 A | 6/1996 | Phelps et al. |
| 5,522,836 A | 6/1996 | Palermo |
| 5,527,338 A | 6/1996 | Purdy |
| 5,536,274 A | 7/1996 | Neuss |
| 5,540,680 A | 7/1996 | Guglielmi et al. |
| 5,549,624 A | 8/1996 | Mirigian et al. |
| 5,562,698 A | 10/1996 | Parker |
| 5,569,245 A | 10/1996 | Ji et al. |
| 5,573,520 A | 11/1996 | Schwartz et al. |
| 5,578,074 A | 11/1996 | Mirigian |
| 5,582,619 A | 12/1996 | Ken |
| 5,601,600 A | 2/1997 | Ton |
| 5,624,449 A | 4/1997 | Pham et al. |
| 5,624,461 A | 4/1997 | Mariant |
| 5,626,599 A | 5/1997 | Bourne et al. |
| 5,634,928 A | 6/1997 | Fischell et al. |
| 5,639,277 A | 6/1997 | Mariant et al. |
| 5,643,254 A | 7/1997 | Scheldrup et al. |
| 5,645,558 A | 7/1997 | Horton et al. |
| 5,645,564 A | 7/1997 | Northrup et al. |
| 5,649,949 A | 7/1997 | Wallace et al. |
| 5,658,308 A | 8/1997 | Snyder |
| 5,662,700 A | 9/1997 | Lazarus |
| 5,669,905 A | 9/1997 | Scheldrup et al. |
| 5,669,931 A | 9/1997 | Kupiecki et al. |
| 5,690,666 A | 11/1997 | Berenstein et al. |
| 5,690,667 A | 11/1997 | Gia |
| 5,690,671 A | 11/1997 | McGurk et al. |
| 5,693,067 A | 12/1997 | Purdy |
| 5,695,517 A | 12/1997 | Marin et al. |
| 5,700,258 A | 12/1997 | Mirigian et al. |
| 5,702,361 A | 12/1997 | Evans et al. |
| 5,718,711 A | 2/1998 | Chee et al. |
| 5,725,534 A | 3/1998 | Rasmussen |
| 5,725,546 A | 3/1998 | Samson |
| 5,725,552 A | 3/1998 | Kotula et al. |
| 5,728,129 A | 3/1998 | Summers et al. |
| 5,733,329 A | 3/1998 | Wallace et al. |
| 5,743,905 A | 4/1998 | Eder et al. |
| 5,746,734 A | 5/1998 | Paul et al. |
| 5,746,769 A | 5/1998 | Ton et al. |
| 5,749,891 A | 5/1998 | Ken et al. |
| 5,749,894 A | 5/1998 | Engelson |
| 5,749,918 A | 5/1998 | Hogendijk et al. |
| 5,759,161 A | 6/1998 | Ogawa et al. |
| 5,766,219 A | 6/1998 | Horton |
| 5,797,953 A | 8/1998 | Tekulve |
| 5,800,426 A | 9/1998 | Goto et al. |
| 5,800,453 A | 9/1998 | Gia et al. |
| 5,800,455 A | 9/1998 | Gia et al. |
| 5,814,062 A | 9/1998 | Sepetka et al. |
| 5,830,230 A | 11/1998 | Berryman et al. |
| 5,833,705 A | 11/1998 | Ken et al. |
| 5,843,118 A | 12/1998 | Gia et al. |
| 5,846,210 A | 12/1998 | Ogawa et al. |
| 5,851,206 A | 12/1998 | Ji et al. |
| 5,853,418 A | 12/1998 | Ken et al. |
| 5,855,578 A | 1/1999 | Guglielmi et al. |
| 5,891,058 A | 4/1999 | Taki et al. |
| 5,891,128 A | 4/1999 | Gia et al. |
| 5,891,130 A | 4/1999 | Palermo et al. |
| 5,891,155 A | 4/1999 | Irie |
| 5,891,192 A | 4/1999 | Murayama et al. |
| 5,895,385 A | 4/1999 | Guglielmi et al. |
| 5,895,391 A | 4/1999 | Farnholtz |
| 5,895,410 A | 4/1999 | Forber et al. |
| 5,895,411 A | 4/1999 | Irie |
| 5,911,731 A | 6/1999 | Pham et al. |
| 5,911,737 A | 6/1999 | Lee et al. |
| 5,916,235 A | 6/1999 | Guido |
| 5,919,187 A | 7/1999 | Guglielmi et al. |
| 5,925,037 A | 7/1999 | Guglielmi et al. |
| 5,925,059 A | 7/1999 | Palermo et al. |
| 5,925,060 A | 7/1999 | Forber |
| 5,925,062 A | 7/1999 | Purdy et al. |
| 5,928,226 A | 7/1999 | Guglielmi et al. |
| 5,935,145 A | 8/1999 | Villar et al. |
| 5,935,148 A | 8/1999 | Villar et al. |
| 5,941,249 A | 8/1999 | Maynard et al. |
| 5,941,888 A | 8/1999 | Wallace et al. |
| 5,944,714 A | 8/1999 | Guglielmi et al. |
| 5,944,733 A | 8/1999 | Engelson |
| 5,947,962 A | 9/1999 | Guglielmi et al. |
| 5,947,963 A | 9/1999 | Guglielmi et al. |

(56) References Cited

U.S. PATENT DOCUMENTS

| | | |
|---|---|---|
| 5,957,948 A | 9/1999 | Mariant |
| 5,964,797 A | 10/1999 | Ho |
| 5,972,019 A | 10/1999 | Engelson et al. |
| 5,976,126 A | 11/1999 | Guglielmi et al. |
| 5,976,131 A | 11/1999 | Guglielmi et al. |
| 5,976,152 A | 11/1999 | Regan et al. |
| 5,976,162 A | 11/1999 | Gia et al. |
| 5,980,514 A | 11/1999 | Kupiecki et al. |
| 5,980,550 A | 11/1999 | Eder et al. |
| 5,980,554 A | 11/1999 | Lenker et al. |
| 5,984,929 A | 11/1999 | Bashiri et al. |
| 5,984,944 A | 11/1999 | Forber et al. |
| 5,989,242 A | 11/1999 | Saadat et al. |
| 6,001,092 A | 12/1999 | Mirigian et al. |
| 6,004,338 A | 12/1999 | Ken et al. |
| 6,010,498 A | 1/2000 | Guglielmi et al. |
| 6,013,084 A | 1/2000 | Ken et al. |
| 6,015,424 A | 1/2000 | Rosenbluth et al. |
| 6,017,364 A | 1/2000 | Lazarus |
| 6,017,977 A | 1/2000 | Evans et al. |
| 6,019,757 A | 2/2000 | Scheldrup |
| 6,022,369 A | 2/2000 | Lippert et al. |
| 6,024,754 A | 2/2000 | Engelson |
| 6,024,765 A | 2/2000 | Wallace et al. |
| 6,030,413 A | 2/2000 | Lazarus |
| 6,033,423 A | 3/2000 | Ken et al. |
| 6,039,744 A | 3/2000 | Forber et al. |
| 6,039,749 A | 3/2000 | Marin et al. |
| 6,056,770 A | 5/2000 | Epstein et al. |
| 6,059,779 A | 5/2000 | Mills |
| 6,059,815 A | 5/2000 | Lee et al. |
| 6,063,070 A | 5/2000 | Eder |
| 6,063,100 A | 5/2000 | Diaz et al. |
| 6,063,104 A | 5/2000 | Villar et al. |
| 6,066,133 A | 5/2000 | Guglielmi et al. |
| 6,066,149 A | 5/2000 | Samson et al. |
| 6,068,644 A | 5/2000 | Lulo et al. |
| 6,074,407 A | 6/2000 | Wallace et al. |
| 6,077,260 A | 6/2000 | Wheelock et al. |
| D427,680 S * | 7/2000 | Mariant ........................ D24/143 |
| 6,083,220 A | 7/2000 | Guglielmi et al. |
| 6,086,577 A | 7/2000 | Ken et al. |
| 6,090,125 A | 7/2000 | Horton |
| 6,093,199 A | 7/2000 | Brown et al. |
| 6,096,034 A | 8/2000 | Kupiecki et al. |
| 6,096,546 A | 8/2000 | Raskin |
| 6,102,917 A | 8/2000 | Maitland et al. |
| 6,102,932 A | 8/2000 | Kurz |
| 6,102,933 A | 8/2000 | Lee et al. |
| 6,113,622 A | 9/2000 | Hieshima |
| 6,117,142 A | 9/2000 | Goodson et al. |
| 6,123,714 A | 9/2000 | Gia et al. |
| 6,126,672 A | 10/2000 | Berryman et al. |
| 6,136,015 A | 10/2000 | Kurz et al. |
| 6,143,007 A | 11/2000 | Mariant et al. |
| 6,146,373 A | 11/2000 | Greff et al. |
| 6,149,644 A | 11/2000 | Xie et al. |
| 6,149,681 A | 11/2000 | Fleischman et al. |
| 6,152,947 A | 11/2000 | Turovskiy et al. |
| 6,156,061 A * | 12/2000 | Wallace ............ A61B 17/12022 606/200 |
| 6,159,165 A | 12/2000 | Ken et al. |
| 6,159,206 A | 12/2000 | Ogawa |
| 6,165,193 A * | 12/2000 | Greene, Jr. ...... A61B 17/12022 606/191 |
| 6,165,198 A | 12/2000 | McGurk et al. |
| 6,168,570 B1 | 1/2001 | Ferrera et al. |
| 6,168,615 B1 * | 1/2001 | Ken ................. A61B 17/12022 623/1.1 |
| 6,168,622 B1 * | 1/2001 | Mazzocchi ........ A61B 17/0057 606/200 |
| 6,171,326 B1 | 1/2001 | Ferrera et al. |
| 6,183,491 B1 | 2/2001 | Lulo et al. |
| 6,187,024 B1 | 2/2001 | Boock et al. |
| 6,187,027 B1 | 2/2001 | Mariant et al. |
| 6,190,373 B1 | 2/2001 | Palermo et al. |
| 6,193,708 B1 * | 2/2001 | Ken ................. A61B 17/12022 606/1 |
| 6,193,728 B1 | 2/2001 | Ken et al. |
| RE37,117 E | 3/2001 | Palermo et al. |
| 6,202,261 B1 | 3/2001 | Tambay et al. |
| 6,203,547 B1 | 3/2001 | Nguyen et al. |
| 6,221,066 B1 * | 4/2001 | Ferrera ............ A61B 17/12022 606/1 |
| 6,224,610 B1 * | 5/2001 | Ferrera ...................... A61F 2/95 606/108 |
| 6,231,573 B1 | 5/2001 | Amor et al. |
| 6,231,586 B1 | 5/2001 | Mariant et al. |
| 6,231,590 B1 | 5/2001 | Slaikeu et al. |
| 6,231,597 B1 * | 5/2001 | Deem ............. A61B 17/12022 606/108 |
| 6,238,403 B1 * | 5/2001 | Greene, Jr. ...... A61B 17/12022 606/108 |
| 6,238,415 B1 | 5/2001 | Sepetka et al. |
| 6,241,691 B1 | 6/2001 | Wilson et al. |
| 6,254,592 B1 | 7/2001 | Samson et al. |
| 6,270,495 B1 | 8/2001 | Palermo et al. |
| 6,270,508 B1 | 8/2001 | Klieman et al. |
| 6,277,125 B1 | 8/2001 | Barry et al. |
| 6,277,126 B1 | 8/2001 | Barry et al. |
| 6,280,457 B1 | 8/2001 | Wallace et al. |
| 6,281,263 B1 | 8/2001 | Evans et al. |
| 6,287,315 B1 * | 9/2001 | Wijeratne ........ A61B 17/12109 606/108 |
| 6,287,318 B1 | 9/2001 | Villar et al. |
| 6,293,960 B1 * | 9/2001 | Ken ................. A61B 17/12113 606/195 |
| 6,296,622 B1 * | 10/2001 | Kurz ................ A61B 17/12022 604/93.01 |
| 6,299,619 B1 | 10/2001 | Greene et al. |
| 6,299,627 B1 | 10/2001 | Eder et al. |
| 6,306,153 B1 | 10/2001 | Kurz et al. |
| 6,312,405 B1 | 11/2001 | Magliochetti et al. |
| 6,312,421 B1 | 11/2001 | Boock et al. |
| 6,315,709 B1 | 11/2001 | Hogg et al. |
| 6,319,267 B1 | 11/2001 | Kurz et al. |
| 6,322,576 B1 * | 11/2001 | Wallace ............ A61B 17/12022 606/191 |
| 6,331,184 B1 | 12/2001 | Abrams et al. |
| 6,335,384 B1 | 1/2002 | Evans et al. |
| 6,344,048 B1 * | 2/2002 | Chin ................ A61B 17/12022 606/159 |
| 6,346,091 B1 | 2/2002 | Jacobsen et al. |
| 6,348,041 B1 | 2/2002 | Klint et al. |
| 6,361,547 B1 | 3/2002 | Hieshima et al. |
| 6,364,823 B1 | 4/2002 | Garibaldi et al. |
| 6,368,338 B1 * | 4/2002 | Konya ............ A61B 17/12022 606/200 |
| 6,371,972 B1 | 4/2002 | Wallace et al. |
| 6,375,606 B1 | 4/2002 | Garibaldi et al. |
| 6,375,628 B1 | 4/2002 | Zadno-Azizi et al. |
| 6,375,668 B1 * | 4/2002 | Gifford ............ A61B 17/12022 606/200 |
| 6,375,669 B1 | 4/2002 | Rosenbluth et al. |
| 6,379,329 B1 | 4/2002 | Naglreiter et al. |
| 6,379,374 B1 | 4/2002 | Hieshima et al. |
| 6,383,146 B1 | 5/2002 | Klint et al. |
| 6,383,204 B1 | 5/2002 | Kurz et al. |
| 6,397,850 B1 | 6/2002 | Scheldrup et al. |
| 6,409,721 B1 | 6/2002 | Wheelock et al. |
| 6,416,535 B1 | 7/2002 | Lazarus et al. |
| 6,416,541 B2 | 7/2002 | Denardo et al. |
| 6,423,085 B1 | 7/2002 | Murayama et al. |
| 6,425,893 B1 | 7/2002 | Guglielmi |
| 6,425,914 B1 | 7/2002 | Wallace et al. |
| 6,428,557 B1 | 8/2002 | Hilaire et al. |
| 6,428,558 B1 | 8/2002 | Jones et al. |
| 6,454,780 B1 | 9/2002 | Wallace |
| 6,458,119 B1 | 10/2002 | Berenstein et al. |
| 6,458,127 B1 | 10/2002 | Truckai et al. |
| 6,458,137 B1 | 10/2002 | Klint et al. |
| 6,464,699 B1 | 10/2002 | Swanson et al. |
| 6,468,266 B1 | 10/2002 | Bashiri et al. |

(56) References Cited

U.S. PATENT DOCUMENTS

| | | |
|---|---|---|
| 6,475,169 B2 | 11/2002 | Ferrera et al. |
| 6,475,227 B2 | 11/2002 | Burke et al. |
| 6,478,773 B1 | 11/2002 | Gandhi et al. |
| 6,485,524 B2 | 11/2002 | Strecker et al. |
| 6,494,884 B2 | 12/2002 | Gifford, III et al. |
| 6,500,149 B2 | 12/2002 | Gandhi et al. |
| 6,500,190 B2 | 12/2002 | Greene et al. |
| 6,506,204 B2 | 1/2003 | Mazzocchi |
| 6,511,468 B1 | 1/2003 | Cragg et al. |
| 6,514,264 B1 | 2/2003 | Naglreiter et al. |
| 6,530,934 B1 | 3/2003 | Jacobsen et al. |
| 6,533,801 B2 | 3/2003 | Wallace et al. |
| 6,537,293 B1 | 3/2003 | Berryman et al. |
| 6,540,657 B2 | 4/2003 | Cross et al. |
| 6,544,163 B2 | 4/2003 | Wallace et al. |
| 6,544,225 B1 | 4/2003 | Lulo et al. |
| 6,544,268 B1 | 4/2003 | Lazarus et al. |
| 6,544,275 B1 | 4/2003 | Teoh et al. |
| 6,547,804 B2 | 4/2003 | Porter et al. |
| 6,551,305 B2 | 4/2003 | Ferrera et al. |
| 6,551,340 B1 | 4/2003 | Kónya et al. |
| 6,554,849 B1 | 4/2003 | Jones et al. |
| 6,558,367 B1 | 5/2003 | Cragg et al. |
| 6,569,179 B2 | 5/2003 | Teoh et al. |
| 6,572,628 B2 | 6/2003 | Dominguez et al. |
| 6,575,994 B1 | 6/2003 | Marin et al. |
| 6,585,748 B1 | 7/2003 | Jeffree |
| 6,585,754 B2 | 7/2003 | Wallace et al. |
| 6,589,227 B2 | 7/2003 | Klint |
| 6,589,230 B2 | 7/2003 | Gia et al. |
| 6,589,236 B2 | 7/2003 | Wheelock et al. |
| 6,589,251 B2 | 7/2003 | Yee et al. |
| 6,589,265 B1 | 7/2003 | Palmer et al. |
| 6,592,605 B2 | 7/2003 | Lenker et al. |
| 6,602,261 B2 | 8/2003 | Greene et al. |
| 6,602,269 B2 | 8/2003 | Wallace et al. |
| 6,603,994 B2 | 8/2003 | Wallace et al. |
| 6,605,101 B1 | 8/2003 | Schaefer et al. |
| 6,607,538 B1 | 8/2003 | Ferrera et al. |
| 6,607,539 B1 | 8/2003 | Hayashi et al. |
| 6,610,085 B1 | 8/2003 | Lazarus et al. |
| 6,613,074 B1 | 9/2003 | Mitelberg et al. |
| 6,616,617 B1 | 9/2003 | Larsen et al. |
| 6,620,152 B2 | 9/2003 | Guglielmi |
| 6,623,493 B2 | 9/2003 | Wallace et al. |
| 6,632,241 B1 | 10/2003 | Hancock et al. |
| 6,635,068 B1 | 10/2003 | Dubrul et al. |
| 6,635,069 B1 | 10/2003 | Teoh et al. |
| 6,638,291 B1 | 10/2003 | Ferrera et al. |
| 6,638,293 B1 | 10/2003 | MacHold et al. |
| 6,656,173 B1 | 12/2003 | Palermo et al. |
| 6,656,201 B2 | 12/2003 | Kurz et al. |
| 6,656,218 B1 | 12/2003 | Denardo et al. |
| 6,656,351 B2 | 12/2003 | Boyle et al. |
| 6,660,020 B2 | 12/2003 | Wallace et al. |
| 6,663,607 B2 | 12/2003 | Slaikeu et al. |
| 6,679,903 B2 | 1/2004 | Kurz et al. |
| 6,685,653 B2 | 2/2004 | Ehr et al. |
| 6,689,141 B2 | 2/2004 | Ferrera et al. |
| 6,692,510 B2 | 2/2004 | West et al. |
| 6,702,844 B1 | 3/2004 | Lazarus et al. |
| 6,716,238 B2 | 4/2004 | Elliott et al. |
| 6,723,112 B2 | 4/2004 | Ho et al. |
| 6,743,236 B2 | 6/2004 | Barry et al. |
| 6,743,251 B1 | 6/2004 | Eder et al. |
| 6,767,358 B2 | 7/2004 | Taheri et al. |
| 6,811,561 B2 | 11/2004 | Diaz et al. |
| 6,814,748 B1 | 11/2004 | Baker et al. |
| 6,835,185 B2 | 12/2004 | Ramzipoor et al. |
| 6,849,081 B2 | 2/2005 | Sepetka et al. |
| 6,852,116 B2 | 2/2005 | Taheri et al. |
| 6,853,418 B2 | 2/2005 | Suzuki et al. |
| 6,855,153 B2 | 2/2005 | Saadat |
| 6,855,155 B2 | 2/2005 | Denardo et al. |
| 6,860,893 B2 | 3/2005 | Wallace et al. |
| 6,860,901 B1 | 3/2005 | Baker et al. |
| 6,872,218 B2 | 3/2005 | Kurz et al. |
| 6,878,163 B2 | 4/2005 | Denardo et al. |
| 6,905,503 B2 | 6/2005 | Gifford et al. |
| 6,913,618 B2 | 7/2005 | Denardo et al. |
| 6,929,654 B2 | 8/2005 | Teoh et al. |
| 6,945,956 B2 | 9/2005 | Waldhauser et al. |
| 6,958,061 B2 | 10/2005 | Truckai et al. |
| 6,958,068 B2 | 10/2005 | Hieshima et al. |
| 6,964,657 B2 | 11/2005 | Pecor et al. |
| 6,966,892 B2 | 11/2005 | Ramzipoor et al. |
| 6,994,689 B1 | 2/2006 | Zadno-Azizi et al. |
| 6,994,711 B2 | 2/2006 | Hieshima et al. |
| 7,014,645 B2 | 3/2006 | Greene et al. |
| 7,018,394 B2 | 3/2006 | Diaz et al. |
| 7,022,133 B2 | 4/2006 | Yee et al. |
| 7,029,486 B2 | 4/2006 | Schaefer et al. |
| 7,029,487 B2 | 4/2006 | Green, Jr. et al. |
| 7,033,374 B2 | 4/2006 | Schaefer et al. |
| 7,058,456 B2 | 6/2006 | Pierce |
| 7,060,083 B2 | 6/2006 | Gerberding et al. |
| 7,070,607 B2 | 7/2006 | Vinuela et al. |
| 7,147,618 B2 | 12/2006 | Kurz et al. |
| 7,169,161 B2 | 1/2007 | Jenson et al. |
| 7,182,774 B2 | 2/2007 | Barry et al. |
| 7,198,613 B2 | 4/2007 | Ramzipoor et al. |
| 7,238,194 B2 | 7/2007 | Monstadt et al. |
| 7,294,146 B2 | 11/2007 | Chew et al. |
| 7,300,458 B2 | 11/2007 | Kontek et al. |
| 7,316,701 B2 | 1/2008 | Ferrera et al. |
| 7,323,000 B2 | 1/2008 | Monstdt et al. |
| 7,331,973 B2 | 2/2008 | Gesswein et al. |
| 7,344,558 B2 | 3/2008 | Lorenzo et al. |
| 7,367,987 B2 | 5/2008 | Balgobin et al. |
| 7,371,252 B2 | 5/2008 | Balgobin et al. |
| 7,377,932 B2 | 5/2008 | Mitelberg et al. |
| 7,410,482 B2 | 8/2008 | Murphy et al. |
| 7,419,501 B2 | 9/2008 | Chiu et al. |
| 7,473,266 B2 | 1/2009 | Glaser et al. |
| 7,485,122 B2 | 2/2009 | Teoh et al. |
| 7,485,317 B1 | 2/2009 | Murayama et al. |
| 7,524,322 B2 | 4/2009 | Monstadt et al. |
| 7,575,582 B2 | 8/2009 | Ramzipoor et al. |
| 7,578,826 B2 | 8/2009 | Gandhi et al. |
| 7,591,829 B2 | 9/2009 | Gibson et al. |
| 7,691,124 B2 | 4/2010 | Balgobin et al. |
| 7,708,755 B2 | 5/2010 | Davis et al. |
| 7,722,636 B2 | 5/2010 | Farnan et al. |
| 7,722,637 B2 | 5/2010 | Barry et al. |
| 7,811,305 B2 | 10/2010 | Balgobin et al. |
| 7,879,064 B2 | 2/2011 | Henkes et al. |
| 7,896,899 B2 | 3/2011 | Slee et al. |
| 7,901,444 B2 | 3/2011 | Slazas et al. |
| 7,918,872 B2 | 4/2011 | Mitelberg et al. |
| 8,007,509 B2 | 8/2011 | Buiser et al. |
| RE42,758 E | 9/2011 | Ken et al. |
| 8,016,852 B2 | 9/2011 | Slaikeu et al. |
| 8,029,466 B2 | 10/2011 | Desai et al. |
| 8,034,073 B2 | 10/2011 | Davis et al. |
| 8,062,325 B2 | 11/2011 | Balgobin et al. |
| 8,100,918 B2 | 1/2012 | Ramzipoor et al. |
| 8,142,456 B2 | 3/2012 | Rosqueta et al. |
| 8,333,796 B2 | 12/2012 | Leynov et al. |
| 9,579,104 B2 * | 2/2017 | Beckham ......... A61B 17/12113 |
| 2001/0002438 A1 | 5/2001 | Sepetka et al. |
| 2001/0037141 A1 | 11/2001 | Yee et al. |
| 2001/0049521 A1 * | 12/2001 | Gia ................. A61B 17/12022 606/1 |
| 2002/0010481 A1 | 1/2002 | Jayaraman et al. |
| 2002/0065529 A1 | 5/2002 | Laurent et al. |
| 2002/0072712 A1 | 6/2002 | Nool et al. |
| 2002/0072791 A1 | 6/2002 | Eder et al. |
| 2002/0082620 A1 | 6/2002 | Lee et al. |
| 2002/0087184 A1 | 7/2002 | Eder et al. |
| 2002/0116024 A1 | 8/2002 | Goldberg et al. |
| 2002/0120297 A1 | 8/2002 | Shadduck |
| 2002/0128671 A1 | 9/2002 | Wallace et al. |
| 2002/0138095 A1 | 9/2002 | Mazzocchi et al. |
| 2002/0143348 A1 | 10/2002 | Wallace et al. |

(56) References Cited

U.S. PATENT DOCUMENTS

| | | |
|---|---|---|
| 2002/0143349 A1 | 10/2002 | Gifford, III et al. |
| 2002/0169473 A1 | 11/2002 | Sepetka et al. |
| 2003/0014073 A1 | 1/2003 | Bashiri et al. |
| 2003/0040733 A1 | 2/2003 | Cragg et al. |
| 2003/0045901 A1 | 3/2003 | Opolski et al. |
| 2003/0083676 A1 | 5/2003 | Wallace |
| 2003/0130689 A1 | 7/2003 | Wallace et al. |
| 2003/0169473 A1 | 9/2003 | Cotter et al. |
| 2003/0171770 A1 | 9/2003 | Kusleika et al. |
| 2003/0176857 A1 | 9/2003 | Lee et al. |
| 2003/0181927 A1 | 9/2003 | Wallace et al. |
| 2003/0199966 A1 | 10/2003 | Shiu et al. |
| 2003/0225365 A1 | 12/2003 | Greff et al. |
| 2004/0002731 A1 | 1/2004 | Aganon et al. |
| 2004/0002732 A1 | 1/2004 | Teoh et al. |
| 2004/0002733 A1 | 1/2004 | Teoh et al. |
| 2004/0024394 A1 | 2/2004 | Wallace et al. |
| 2004/0034363 A1 | 2/2004 | Wilson et al. |
| 2004/0087964 A1 | 5/2004 | Diaz et al. |
| 2004/0106946 A1 | 6/2004 | Ferrera et al. |
| 2004/0181256 A1 | 9/2004 | Glaser et al. |
| 2004/0193178 A1 | 9/2004 | Nikolchev et al. |
| 2004/0193206 A1 | 9/2004 | Gerberding et al. |
| 2004/0220563 A1 | 11/2004 | Eder et al. |
| 2004/0220585 A1 | 11/2004 | Nikolchev et al. |
| 2004/0225279 A1 | 11/2004 | Raymond et al. |
| 2004/0243228 A1 | 12/2004 | Kowalsky et al. |
| 2005/0021023 A1 | 1/2005 | Guglielmi et al. |
| 2005/0079196 A1 | 4/2005 | Henkes et al. |
| 2006/0025792 A1 | 2/2006 | Gibson et al. |
| 2006/0025801 A1 | 2/2006 | Lulo et al. |
| 2006/0025802 A1 | 2/2006 | Sowers et al. |
| 2006/0036281 A1 | 2/2006 | Patterson et al. |
| 2006/0079926 A1 | 4/2006 | Desai et al. |
| 2006/0106417 A1 | 5/2006 | Tessmer et al. |
| 2006/0116714 A1 | 6/2006 | Sepetka et al. |
| 2006/0271097 A1 | 11/2006 | Ramzipoor et al. |
| 2006/0271099 A1 | 11/2006 | Marks et al. |
| 2006/0276823 A1 | 12/2006 | Mitelberg et al. |
| 2006/0276824 A1 | 12/2006 | Mitelberg et al. |
| 2006/0278680 A1 | 12/2006 | Viola et al. |
| 2007/0055302 A1 | 3/2007 | Henry et al. |
| 2007/0173757 A1 | 7/2007 | Levine et al. |
| 2007/0179520 A1 | 8/2007 | West |
| 2007/0185524 A1 | 8/2007 | Diaz et al. |
| 2007/0221230 A1 | 9/2007 | Thompson et al. |
| 2007/0239193 A1 | 10/2007 | Simon et al. |
| 2007/0265656 A1 | 11/2007 | Amplatz et al. |
| 2007/0267281 A1 | 11/2007 | Smith et al. |
| 2007/0270936 A1 | 11/2007 | Andreas et al. |
| 2007/0282373 A1 | 12/2007 | Ashby et al. |
| 2008/0045922 A1 | 2/2008 | Cragg et al. |
| 2008/0045997 A1 | 2/2008 | Balgobin et al. |
| 2008/0051803 A1 | 2/2008 | Monjtadt et al. |
| 2008/0097462 A1 | 4/2008 | Mitelberg et al. |
| 2008/0103585 A1 | 5/2008 | Monstadt et al. |
| 2008/0119886 A1 | 5/2008 | Greenhalgh et al. |
| 2008/0119887 A1 | 5/2008 | Que et al. |
| 2008/0125855 A1 | 5/2008 | Henkes et al. |
| 2008/0228215 A1 | 9/2008 | Strauss et al. |
| 2008/0228216 A1 | 9/2008 | Strauss et al. |
| 2008/0243106 A1 | 10/2008 | Coe et al. |
| 2008/0255542 A1 | 10/2008 | Nimgaard et al. |
| 2008/0281350 A1 | 11/2008 | Sepetka et al. |
| 2008/0300616 A1 | 12/2008 | Que et al. |
| 2008/0306504 A1 | 12/2008 | Win et al. |
| 2008/0319532 A1 | 12/2008 | Monstadt et al. |
| 2009/0012554 A1 | 1/2009 | Makower et al. |
| 2009/0018653 A1 | 1/2009 | Bashiri et al. |
| 2009/0024154 A1 | 1/2009 | Williams et al. |
| 2009/0062812 A1 | 3/2009 | Fitz et al. |
| 2009/0076623 A1 | 3/2009 | Mathis et al. |
| 2009/0088832 A1 | 4/2009 | Chew et al. |
| 2009/0138036 A1 | 5/2009 | Nardone et al. |
| 2009/0163780 A1 | 6/2009 | Tieu et al. |
| 2009/0163986 A1 | 6/2009 | Tieu et al. |
| 2009/0177261 A1 | 7/2009 | Teoh et al. |
| 2009/0182268 A1 | 7/2009 | Thielen et al. |
| 2009/0254111 A1 | 10/2009 | Monstadt et al. |
| 2009/0254169 A1 | 10/2009 | Spenser et al. |
| 2009/0270877 A1 | 10/2009 | Johnson et al. |
| 2009/0287291 A1 | 11/2009 | Becking et al. |
| 2009/0312748 A1 | 12/2009 | Johnson et al. |
| 2010/0004673 A1 | 1/2010 | Denison et al. |
| 2010/0023105 A1 | 1/2010 | Levy et al. |
| 2010/0030200 A1 | 2/2010 | Strauss et al. |
| 2010/0049165 A1 | 2/2010 | Sutherland et al. |
| 2010/0076476 A1 | 3/2010 | To et al. |
| 2010/0076479 A1* | 3/2010 | Monstadt ......... A61B 17/12022 606/191 |
| 2010/0094395 A1 | 4/2010 | Kellett et al. |
| 2010/0121350 A1* | 5/2010 | Mirigian ......... A61B 17/12022 606/142 |
| 2010/0174269 A1 | 7/2010 | Tompkins et al. |
| 2010/0234872 A1* | 9/2010 | Guo ................ A61B 17/12022 606/191 |
| 2010/0256666 A1 | 10/2010 | Chen et al. |
| 2010/0268204 A1 | 10/2010 | Tieu et al. |
| 2010/0268251 A1 | 10/2010 | Chen et al. |
| 2010/0268252 A1 | 10/2010 | Chen et al. |
| 2010/0324072 A1 | 12/2010 | Chiang et al. |
| 2011/0022003 A1 | 1/2011 | Tekulve et al. |
| 2011/0098814 A1 | 4/2011 | Monstadt et al. |
| 2011/0106098 A1 | 5/2011 | Williams et al. |
| 2011/0106128 A1 | 5/2011 | Chen et al. |
| 2011/0118772 A1 | 5/2011 | Chen et al. |
| 2011/0118776 A1 | 5/2011 | Chen et al. |
| 2011/0118777 A1 | 5/2011 | Patterson et al. |
| 2011/0172700 A1 | 7/2011 | Bose et al. |
| 2011/0202085 A1 | 8/2011 | Loganathan et al. |
| 2011/0208227 A1 | 8/2011 | Becking |
| 2011/0265943 A1 | 11/2011 | Rosqueta et al. |
| 2011/0282380 A1 | 11/2011 | Davis et al. |
| 2011/0301686 A1 | 12/2011 | Bowman et al. |
| 2011/0313447 A1 | 12/2011 | Strauss et al. |
| 2011/0319926 A1 | 12/2011 | Becking et al. |
| 2012/0041470 A1 | 2/2012 | Shrivastava et al. |
| 2012/0041472 A1 | 2/2012 | Tan et al. |
| 2012/0046687 A1 | 2/2012 | Trommeter et al. |
| 2012/0065720 A1 | 3/2012 | Strauss et al. |
| 2012/0101510 A1 | 4/2012 | Lenker et al. |
| 2012/0226305 A1 | 9/2012 | Strauss et al. |
| 2012/0313447 A1 | 12/2012 | Park et al. |
| 2012/0316598 A1 | 12/2012 | Becking et al. |
| 2012/0330347 A1 | 12/2012 | Becking et al. |
| 2013/0066360 A1 | 3/2013 | Becking et al. |
| 2013/0085520 A1 | 4/2013 | Liang et al. |
| 2013/0085521 A1 | 4/2013 | Lim et al. |
| 2013/0085522 A1 | 4/2013 | Becking et al. |
| 2013/0123830 A1 | 5/2013 | Becking et al. |
| 2013/0211495 A1 | 8/2013 | Halden et al. |
| 2013/0331883 A1 | 12/2013 | Strauss et al. |

FOREIGN PATENT DOCUMENTS

| | | |
|---|---|---|
| CN | 1668250 | 9/2005 |
| CN | 101234034 | 8/2008 |
| CN | 101835430 | 9/2010 |
| CN | 102119004 | 7/2011 |
| DE | 4445715 A1 | 6/1996 |
| DE | 19547617 | 9/1997 |
| DE | 19607451 A1 | 9/1997 |
| DE | 19610333 A1 | 9/1997 |
| DE | 19647280 A1 | 10/1997 |
| DE | 19952387 A1 | 5/2001 |
| DE | 10010840 A1 | 9/2001 |
| DE | 10118017 A1 | 10/2002 |
| DE | 10155191 A1 | 5/2003 |
| DE | 69627243 T2 | 1/2004 |
| EP | 707830 A1 | 4/1996 |
| EP | 711532 A1 | 5/1996 |
| EP | 717969 A2 | 6/1996 |
| EP | 720838 A1 | 7/1996 |
| EP | 765636 A3 | 7/1997 |

(56) References Cited

FOREIGN PATENT DOCUMENTS

| | | |
|---|---|---|
| EP | 820726 A2 | 1/1998 |
| EP | 829236 A1 | 3/1998 |
| EP | 830873 A2 | 3/1998 |
| EP | 832607 A1 | 4/1998 |
| EP | 853955 A1 | 7/1998 |
| EP | 865773 A1 | 9/1998 |
| EP | 882428 A2 | 12/1998 |
| EP | 904737 A1 | 3/1999 |
| EP | 914807 A2 | 5/1999 |
| EP | 941700 A1 | 9/1999 |
| EP | 941701 A1 | 9/1999 |
| EP | 992220 A1 | 4/2000 |
| EP | 996372 A1 | 5/2000 |
| EP | 1005837 A2 | 6/2000 |
| EP | 1120088 A1 | 8/2001 |
| EP | 1125553 A1 | 8/2001 |
| EP | 1129666 A1 | 9/2001 |
| EP | 1142535 A2 | 10/2001 |
| EP | 1169969 A1 | 1/2002 |
| EP | 1188413 A2 | 3/2002 |
| EP | 1188414 A1 | 3/2002 |
| EP | 1312312 A1 | 5/2003 |
| EP | 1316293 A2 | 6/2003 |
| EP | 1358850 A2 | 11/2003 |
| EP | 1400208 A1 | 3/2004 |
| EP | 996372 B1 | 9/2004 |
| EP | 1487526 A1 | 12/2004 |
| EP | 1621150 A2 | 2/2006 |
| EP | 1669032 A2 | 6/2006 |
| EP | 1738698 A2 | 1/2007 |
| EP | 1487526 A1 | 9/2010 |
| JP | 6246004 | 9/1994 |
| JP | 7155331 | 6/1995 |
| JP | 7265431 | 10/1995 |
| JP | 7284534 | 10/1995 |
| JP | 09149904 | 6/1997 |
| JP | 9168541 | 6/1997 |
| JP | 1147138 | 6/1999 |
| JP | 1176249 | 7/1999 |
| JP | 2001513389 | 9/2001 |
| JP | 2002523172 | 7/2002 |
| JP | 2004500929 | 1/2004 |
| JP | 2004073874 | 3/2004 |
| JP | 2004267749 | 9/2004 |
| JP | 2006051349 | 2/2006 |
| JP | 2008525113 | 7/2008 |
| JP | 2009533202 | 9/2009 |
| WO | 1988003817 A1 | 6/1988 |
| WO | 1989006984 | 8/1989 |
| WO | 1990012616 A1 | 11/1990 |
| WO | 1991013592 A1 | 9/1991 |
| WO | 1992014408 A1 | 9/1992 |
| WO | 1992021400 A1 | 12/1992 |
| WO | 1993011719 | 6/1993 |
| WO | 1993016650 | 9/1993 |
| WO | 1994006502 | 3/1994 |
| WO | 1994006503 | 3/1994 |
| WO | 1994010936 | 5/1994 |
| WO | 1994011051 | 5/1994 |
| WO | 1994026175 A1 | 11/1994 |
| WO | 1995012367 A1 | 5/1995 |
| WO | 1996018343 A1 | 6/1996 |
| WO | 1996032153 | 10/1996 |
| WO | 1996039950 A1 | 12/1996 |
| WO | 1997027888 A1 | 8/1997 |
| WO | 1997042881 A1 | 11/1997 |
| WO | 1998009570 A1 | 3/1998 |
| WO | 1998017183 A1 | 4/1998 |
| WO | 1998033452 A1 | 8/1998 |
| WO | 1998034546 A1 | 8/1998 |
| WO | 1998039048 A1 | 9/1998 |
| WO | 1998058590 A1 | 12/1998 |
| WO | 1999002094 A1 | 1/1999 |
| WO | 1999005977 A1 | 2/1999 |
| WO | 1999007292 A1 | 2/1999 |
| WO | 1999009893 A1 | 3/1999 |
| WO | 1999032037 A1 | 7/1999 |
| WO | 1999042038 A1 | 8/1999 |
| WO | 1999044538 A1 | 9/1999 |
| WO | 1999049812 | 10/1999 |
| WO | 1999056636 A1 | 2/2000 |
| WO | 2000012016 A1 | 3/2000 |
| WO | 2000013593 A1 | 3/2000 |
| WO | 2000025680 A1 | 5/2000 |
| WO | 2000044306 A1 | 8/2000 |
| WO | 2000072781 A1 | 12/2000 |
| WO | 2001032085 A1 | 5/2001 |
| WO | 2001056500 A2 | 8/2001 |
| WO | 2001058365 A1 | 8/2001 |
| WO | 2001058382 | 8/2001 |
| WO | 2001087184 A1 | 11/2001 |
| WO | 2001093937 A2 | 11/2001 |
| WO | 2002002018 A1 | 1/2002 |
| WO | 2002013705 A1 | 2/2002 |
| WO | 2002013706 A2 | 2/2002 |
| WO | 2002032496 A1 | 4/2002 |
| WO | 2002039911 A2 | 5/2002 |
| WO | 2002041753 A2 | 5/2002 |
| WO | 2002045596 A2 | 6/2002 |
| WO | 2002054943 A2 | 7/2002 |
| WO | 2002072168 A2 | 9/2002 |
| WO | 2002087449 A1 | 11/2002 |
| WO | 2002087651 A1 | 11/2002 |
| WO | 2002089676 A2 | 11/2002 |
| WO | 2002096273 A2 | 12/2002 |
| WO | 2002096301 A2 | 12/2002 |
| WO | 2003001970 A2 | 1/2003 |
| WO | 2003007823 A1 | 1/2003 |
| WO | 2003017852 A1 | 3/2003 |
| WO | 2003034927 A1 | 5/2003 |
| WO | 2003039624 A2 | 5/2003 |
| WO | 2003041615 A1 | 5/2003 |
| WO | 2003053257 A1 | 7/2003 |
| WO | 2003053281 A1 | 7/2003 |
| WO | 2003073914 | 9/2003 |
| WO | 2003077776 A1 | 9/2003 |
| WO | 2003077984 | 9/2003 |
| WO | 2003082128 | 10/2003 |
| WO | 2003086240 | 10/2003 |
| WO | 2003092547 | 11/2003 |
| WO | 2003099370 | 12/2003 |
| WO | 2004008974 A1 | 1/2004 |
| WO | 2004014239 A1 | 2/2004 |
| WO | 2004069059 A2 | 8/2004 |
| WO | 2004073529 A2 | 9/2004 |
| WO | 2004087006 A3 | 11/2004 |
| WO | 2006069123 A1 | 6/2006 |
| WO | 2007070797 A2 | 6/2007 |
| WO | 2007121405 A2 | 10/2007 |
| WO | 2008112435 A2 | 9/2008 |
| WO | 2008112436 A2 | 9/2008 |
| WO | 2008127525 A1 | 10/2008 |
| WO | 2010009019 A1 | 1/2010 |
| WO | 2010117883 | 10/2010 |
| WO | 2010123821 A1 | 10/2010 |

\* cited by examiner

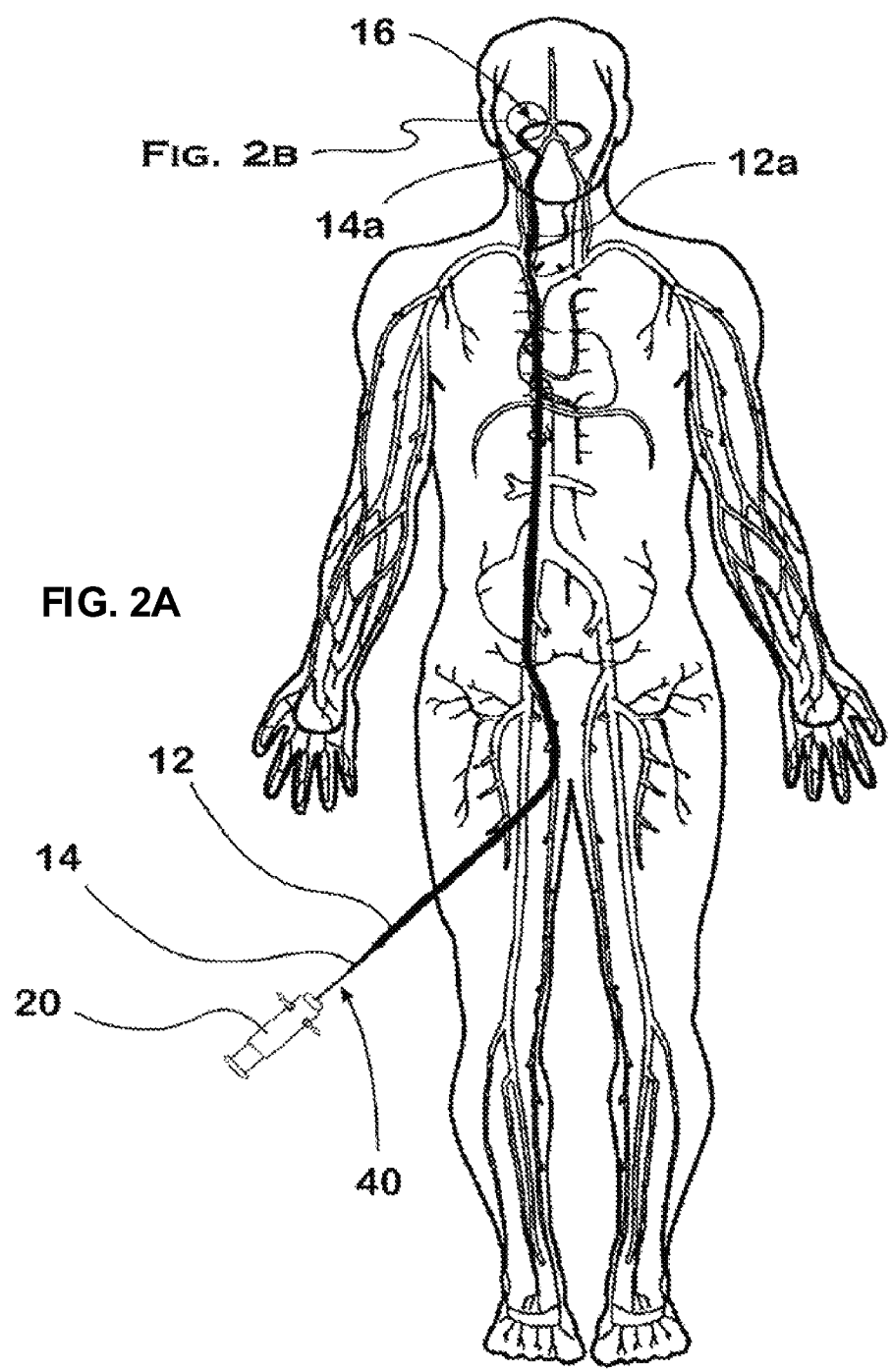

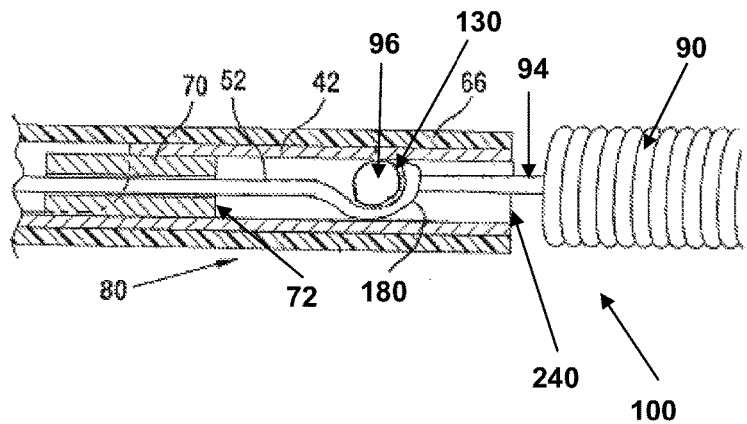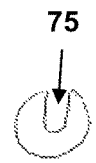
FIG. 9A  FIG. 9B
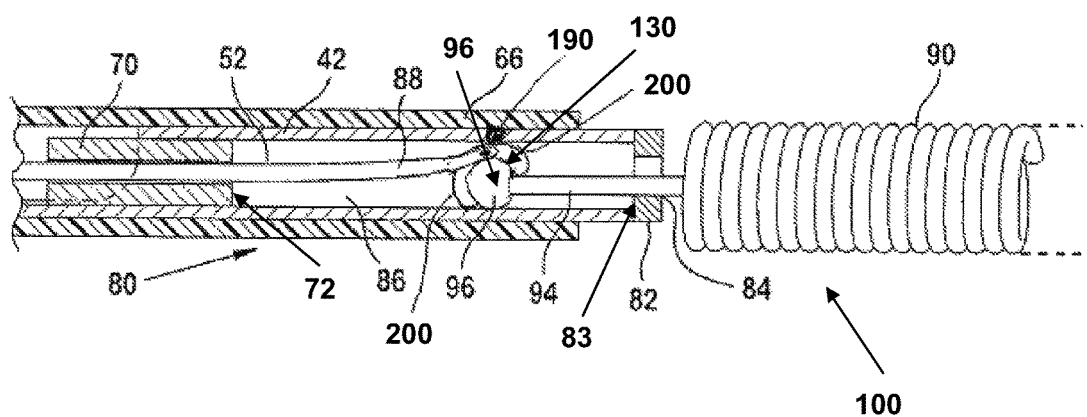
FIG. 10

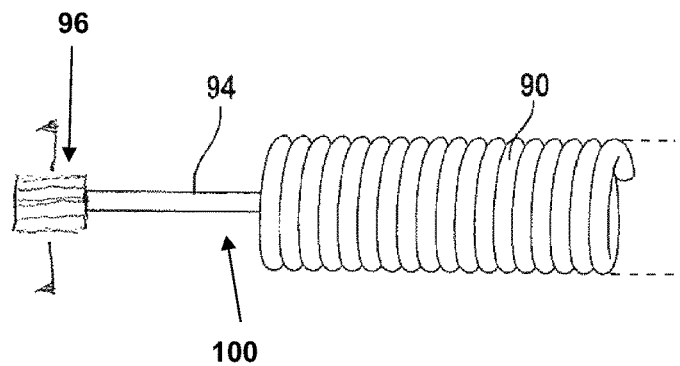 
FIG. 13A  FIG. 13B
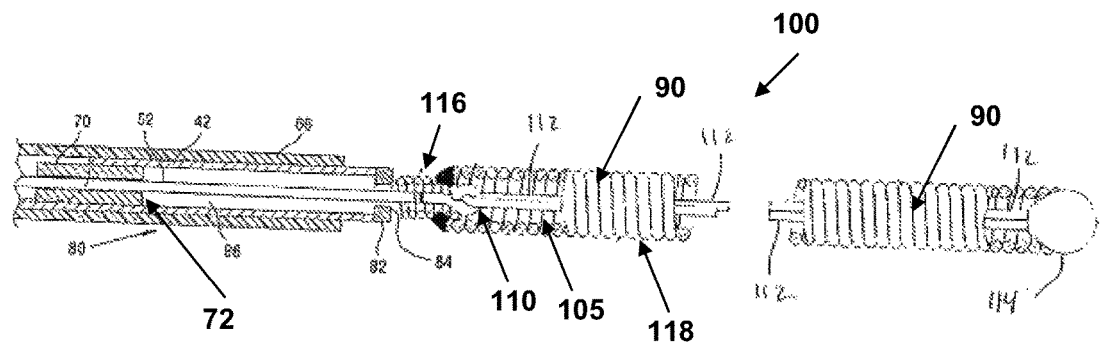
FIG. 14

POSITIONING AND DETACHING IMPLANTS

CROSS-REFERENCE TO RELATED APPLICATION

This application is a divisional of U.S. patent application Ser. No. 13/308,476, filed Nov. 30, 2011, the disclosure of which is incorporated herein by reference in its entirety.

TECHNICAL FIELD

The subject technology relates to therapeutic implant delivery systems and, more particularly, to a system that positions, deploys, and detaches an implant at a target location inside a body.

BACKGROUND

Sometimes a body cavity, such as an aneurysm, is located in a surgically remote and delicate region, such as within the tortuous cerebral vasculature, that requires a specialized delivery system to navigate to the region and safely and reliably deliver and deploy an implant.

SUMMARY

Medical implants are important for their therapeutic and/or intervening roles in patients suffering from various ailments. For example, inferior vena cava filters may be implanted into the inferior vena cava to prevent fatal pulmonary emboli. Dilation balloons may be used during angioplasty procedures in order to widen the vessel and provide structural support.

While there are many known implant detach mechanisms such as electrolytic separation, hydraulic delivery, and interference wire, these systems and methods often suffer from some reliability (e.g., false positive detachments) and/or performance issues (e.g., rigid profiles that are difficult to push).

Therefore, there is a need to provide alternative implant delivery systems and methods that are reliable and overcome existing performance issues.

Although at least some embodiments are described herein with respect to embolic coils, the subject technology may be used to position and deliver a wide variety of medical devices, such as stents, filters, dilation balloons, thrombectomy devices, atherectomy devices, flow restoration devices, embolic coils, embolic protection devices, or other devices to sites within the body.

In clinical situations it may be desirable to occlude blood vessels for various reasons, such as the control or prevention of bleeding, the prevention of blood supply to tumors, treatment of arterial venous malformations (AVMs), and the blocking of blood flow within an aneurysm. Embolization of blood vessels has been performed by employing certain polymer compositions, particulates, and/or sclerosing material including silicone balloons, metallic coils, PVA particles, gelatin, alcohol, and the like, selectively to block blood flow in the blood vessels.

Intracranial aneurysms are abnormal blood-filled dilations of a blood vessel wall that may rupture, causing significant bleeding and damage to surrounding brain tissue or death. In some cases, intracranial aneurysms can be surgically clipped to reduce the risk of rupture by placing a metal clip around the neck of the aneurysm to cut off and prevent further blood flow to the aneurysm. Many aneurysms cannot be treated surgically because of either the location and configuration of the aneurysm or because the condition of the patient does not permit intracranial surgery.

Aneurysms may also be treated endovascularly, e.g., with embolic coils. The coils are placed in the aneurysm by extending a catheter endovascularly to the site of the aneurysm and passing single or often multiple metallic coils such as platinum, stainless steel, or tungsten coils through the catheter into the aneurysm. The coils placed within the aneurysm cause a thrombus to form in the vicinity of the coil which occludes the aneurysm and prevents further blood flow to the aneurysm. The treatment of intracranial aneurysms with coils isolates the aneurysm from arterial circulation, helping to guard against rupture and further growth of the aneurysm.

The subject technology is illustrated, for example, according to various aspects described below. Various examples of aspects of the subject technology are described as embodiments. These are provided as examples and do not limit the subject technology. It is noted that these embodiments may be combined in any combination.

In some embodiments, an assembly for deploying an implant into an aneurysm, comprises: a tubular member having (a) a member lumen in the tubular member and (b) an opening at a distal end portion of the tubular member; a coil implant configured for placement into an aneurysm and having (a) a coil; (b) a coil lumen extending longitudinally within the coil; and (c) a securing member (i) extending within the coil lumen, (ii) coupled, at a distal region of the securing member, to the coil, and (iii) having an enlarged proximal portion larger than, and positioned distal to, the opening; and an elongate member extending in the member lumen, through the opening, and coupled to the enlarged portion; wherein proximal movement of the elongate member relative to the distal end portion results in the enlarged portion contacting the distal end portion and separating from the elongate member.

In some embodiments, the enlarged portion is substantially spherical.

In some embodiments, the separating of the enlarged portion from the elongate member occurs at a location within the enlarged portion. In some embodiments, the separating comprises breaking the elongate member. In certain embodiments, the separating comprises breaking the elongate member at the location.

In some embodiments, the assembly further comprises a stop element, coupled to the elongate member and residing in the member lumen, the stop element contacting the distal end portion upon distal movement of the elongate member relative to the tubular member. In certain embodiments, the stop element is larger than the opening. In certain embodiments, the stop element is substantially spherical.

Some embodiments provide a frictional coupling between the elongate member and the enlarged portion. In some embodiments, separation between the elongate member and the enlarged portion occurs when a force applied to the elongate member during the proximal movement exceeds a force maintaining the frictional coupling. In some embodiments, the separating comprises sliding the elongate member out of the enlarged portion. In certain embodiments, the sliding comprises sliding the elongate member out of an aperture in the enlarged portion In some embodiments, the elongate member extends distally beyond the enlarged portion. In some embodiments, the elongate member extends through the enlarged portion. In certain embodiments, the elongate member, distal to the enlarged portion, has an undulating profile. In certain embodiments, the elongate member, distal to the enlarged portion, has a profile having a pattern of peaks. In certain embodiments, the elongate member, distal to the enlarged portion, extends helically.

In some embodiments, the elongate member has (i) a frictional coupling with the enlarged portion and (ii) an undulating profile distal to the enlarged portion. In some embodiments, the elongate member, distal to the enlarged portion, comprises a shape memory material.

In some embodiments, the separating occurs when a force of the proximal movement exceeds both (a) a force maintaining the frictional coupling and (b) a force required to change the undulating profile as the elongate member is drawn proximally past the enlarged portion.

In some embodiments, the enlarged portion comprises a proximal coil portion having a proximal lumen, and the elongate member extends through the proximal lumen. In certain embodiments, the coil portion is crimped on the elongate member, forming a frictional coupling between the coil portion and the elongate member. In certain embodiments, the separating occurs when a force applied to the elongate member during the proximal movement exceeds a force maintaining the frictional coupling.

Some embodiments provide a method for deploying an implant into an aneurysm, comprising: advancing in a patient's vasculature: (i) a tubular member comprising (a) a member lumen in the tubular member and (b) an opening at a distal end portion of the tubular member; (ii) a coil implant configured for placement into an aneurysm and comprising (a) a coil; (b) a coil lumen extending longitudinally within the coil; and (c) a securing member (i) extending within the coil lumen, (ii) coupled, at a distal region of the securing member, to the coil, and (iii) having an enlarged proximal portion larger than, and positioned distal to, the opening; and (iii) an elongate member extending in the member lumen, through the opening, and coupled to the enlarged portion; and withdrawing the elongate member proximally relative to the tubular member, to release the coil at an aneurysm, the enlarged portion thereby (i) contacting the end portion and (ii) separating from the elongate member.

In some embodiments, the separating of the enlarged portion from the elongate member occurs at a location within the enlarged portion. In certain embodiments, the separation of the enlarged portion and the elongate member comprises breaking the elongate member. In certain embodiments, the step of separating comprises breaking the elongate member within the enlarged portion. In some embodiments, the separating step occurs when a force applied to the elongate member during the proximal movement exceeds a force maintaining a frictional coupling between the elongate member and the enlarged portion. In certain embodiments, the separating step in some methods comprises pulling the elongate member from within the enlarged portion. In certain embodiments, the separating step comprises withdrawing a distal segment of the elongate member through the enlarged portion, the segment having a curved profile. In certain embodiments, the curved profile comprises a wave profile.

Some embodiments provide a method, of forming an attachment coupling of an implant assembly, comprising: plastically deforming a proximal portion of a coil implant, implantable in an aneurysm onto an elongate member to create a friction coupling between the proximal portion and the elongate member; wherein the proximal portion is positioned distal to an opening at a distal end portion of a tubular member through which the elongate member extends.

In certain embodiments, the deforming comprises crimping. In certain embodiments, the deforming comprises swaging.

Some embodiments provide a method, of forming an attachment coupling of an implant assembly, comprising: forming a joint between a proximal portion of a coil implant, implantable in an aneurysm, and an elongate member; wherein a tensile strength of the joint is less than (a) a tensile strength of the proximal portion and (b) a tensile strength of the elongate member; wherein the coupling proximal portion is positioned distal to an opening at a distal end portion of a tubular member through which the elongate member extends.

In certain embodiments, the forming comprises welding.
In certain embodiments, the forming comprises soldering.

Some embodiments provide an assembly for deploying an implant into an aneurysmal space in a vessel in a patient's body, comprising: a tubular member having (a) a member lumen in the tubular member and (b) an opening at a distal end portion of the tubular member; a coil implant having an enlarged portion positioned in the member lumen proximal to the opening; and an elongate member extending in the lumen, the elongate member having a distal segment that extends, in the member lumen, past part of the enlarged portion and contacts a distal-facing surface of the enlarged portion, thereby retaining the enlarged portion in the member lumen; wherein proximal movement of the elongate member relative to the end portion results in deformation of the distal segment to release the enlarged portion from the member lumen.

In certain embodiments, the enlarged portion is substantially spherical. In certain embodiments, the segment extends around part of the enlarged portion. In certain embodiments, the opening is sized to prevent passage of the distal segment through the opening.

In some embodiments, the coil implant comprises a coil having a lumen and a securing member (i) extending within the coil lumen, (ii) coupled, at a distal region of the securing member, to the coil, and (iii) coupled, at a proximal region of the securing member, to the enlarged portion. In certain embodiments, the releasing occurs as the distal segment slides between the enlarged portion and the tubular member. In certain embodiments, the distal segment extends around opposed surfaces of the enlarged portion. In certain embodiments, the distal segment forms a socket that receives the enlarged portion.

In some embodiments, the assembly further comprises a stop element, coupled to the securing member and residing distal to the opening, the stop element contacting the distal end portion upon proximal movement of the elongate member relative to the tubular member. In certain embodiments, the stop element is larger than the opening. In certain embodiments, the stop element comprises a coil. In certain embodiments, the stop element is substantially spherical.

In some embodiments, the releasing occurs by the distal segment pivoting, within the lumen, about the enlarged portion. In certain embodiments, the pivoting results in the distal segment losing contact with the distal-facing surface. In certain embodiments, the releasing occurs by the distal segment tilting within the lumen.

In some embodiments, the distal segment comprises a slot that receives, within the lumen, a portion of the coil implant distal to the enlarged portion. In certain embodiments, the distal segment covers substantially the entire distal-facing surface.

In some embodiments, the coil implant comprises a coil having a lumen and a securing member (i) extending within the coil lumen, (ii) coupled, at a distal region of the securing member, to the coil, and (iii) coupled, at a proximal region of the securing member, to the enlarged portion; and the distal segment comprises a slot that receives, within the lumen, a portion of the securing member.

In certain embodiments, the distal segment covers substantially the entire distal-facing surface.

Some embodiments provide a method for deploying an implant into an aneurysm, comprising: positioning in a patient's vasculature: (i) a tubular member having (a) a member lumen in the tubular member and (b) an opening at a distal end portion of the tubular member; (ii) a coil implant having an enlarged portion positioned in the member lumen proximal to the opening; and (iii) an elongate member extending in the lumen, the elongate member having a distal segment that extends past part of the enlarged portion, in the member lumen, and contacts a distal-facing surface of the enlarged portion, thereby retaining the enlarged portion in the member lumen; and moving the elongate member proximally relative to the tubular member to deform the distal segment, thereby releasing the enlarged portion from the member lumen.

Some embodiments provide a system for placing an implant in an aneurysm, comprising: a tubular member having (a) a member lumen in the tubular member and (b) an opening at a distal end portion of the tubular member; a coil implant configured for placement in an aneurysm and having an enlarged portion positioned in the member lumen proximal to the opening; and a elongate member extending in the lumen and having an expandable body (a) positioned at least partially distal to the enlarged portion in the lumen and (b) expandable distal to the enlarged portion to retain the enlarged portion in the lumen.

In certain embodiments, the expandable body comprises a mesh. In certain embodiments, the expandable body comprises a balloon.

In some embodiments, a proximal movement of the elongate member relative to the tubular member, the body compresses and moves past the enlarged portion, thereby releasing the coil implant from the tubular member. In certain embodiments, the enlarged portion is substantially spherical.

Additional features and advantages of the subject technology will be set forth in the description below, and in part will be apparent from the description, or may be learned by practice of the subject technology. The advantages of the subject technology will be realized and attained by the structure particularly pointed out in the written description and claims hereof as well as the appended drawings.

It is to be understood that both the foregoing general description and the following detailed description are exemplary and explanatory and are intended to provide further explanation of the subject technology as claimed.

BRIEF DESCRIPTION OF THE DRAWINGS

The accompanying drawings, which are included to provide further understanding of the subject technology and are incorporated in and constitute a part of this specification, illustrate aspects of the subject technology and together with the description serve to explain the principles of the subject technology.

FIG. 2A shows a plan view of the position system of FIG. 1A within the human body.

FIG. 9A shows a closer view of a portion of an exemplary implant interface in accordance with some embodiments of the subject technology.

FIG. 9B shows an end view of a component of an exemplary implant interface in accordance with some embodiments of the subject technology.

FIG. 10 shows a closer view of a portion of an exemplary implant interface in accordance with some embodiments of the subject technology.

FIG. 13A shows a closer view of a portion of an exemplary implant in accordance with some embodiments of the subject technology.

FIG. 13B shows a cross-section view of an exemplary implant in accordance with some embodiments of the subject technology.

FIG. 14 shows a closer view of a portion of an exemplary implant in accordance with some embodiments of the subject technology.

DETAILED DESCRIPTION

In the following detailed description, numerous specific details are set forth to provide a full understanding of the subject technology. It will be apparent, however, to one ordinarily skilled in the art that the subject technology may be practiced without some of these specific details. In other instances, well-known structures and techniques have not been shown in detail so as not to obscure the subject technology.

A phrase such as "an aspect" does not imply that such aspect is essential to the subject technology or that such aspect applies to all configurations of the subject technology. A disclosure relating to an aspect may apply to all configurations, or one or more configurations. An aspect may provide one or more examples of the disclosure. A phrase such as "an aspect" may refer to one or more aspects and vice versa. A phrase such as "an embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples of the disclosure. A phrase such "an embodiment" may refer to one or more embodiments and vice versa. A phrase such as "a configuration" does not imply that such configuration is essential to the subject technology or that such configuration applies to all configurations of the subject technology. A disclosure relating to a configuration may apply to all configurations, or one or more configurations. A configuration may provide one or more examples of the disclosure. A phrase such as "a configuration" may refer to one or more configurations and vice versa.

While the preferred embodiments of the subject technology relate to vasculature implant systems and means of deploying an implant in a vasculature, the systems and methods of this disclosure may generally be used for or in conjunction with any systems or methods that are compatible with mechanical detachment mechanisms as described herein.

Figure 1A:
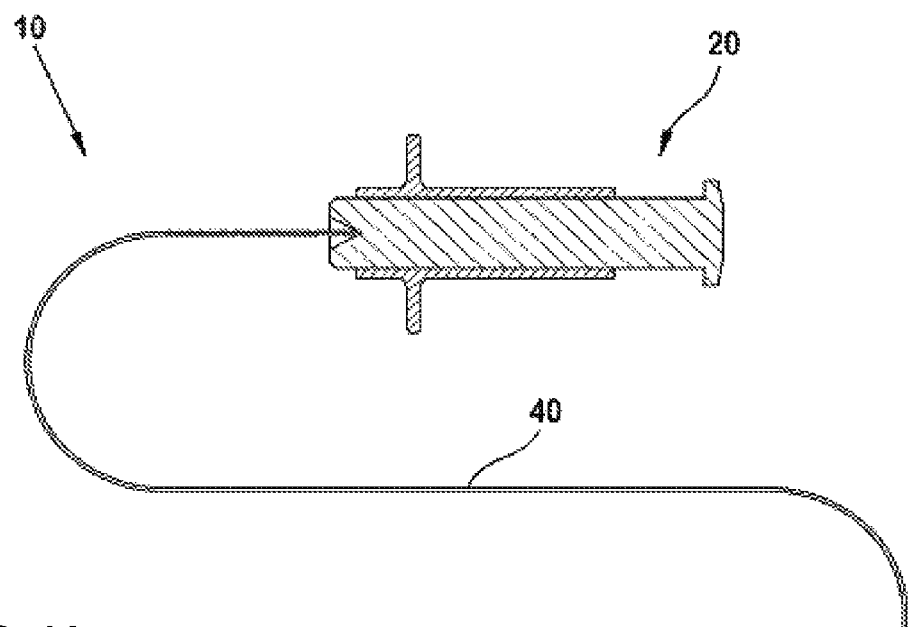
FIG. 1A shows a plan view of the positioning system in accordance with some embodiments of the subject technology, and a plan view of an exemplary implant in accordance with some embodiments of the subject technology.
Figure 1B:
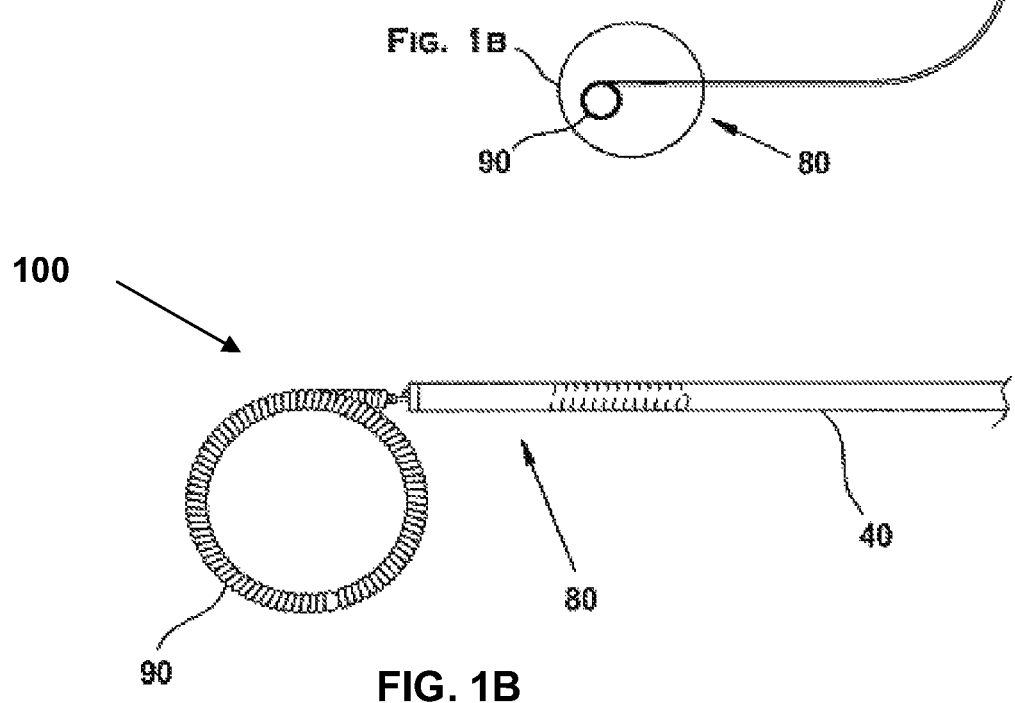
FIG. 1B shows a closer view of a portion of FIG. 1A.

A vascular implant device may be a positioning system 10 such as one shown in FIGS. 1A-1B. The positioning system 10 shown in FIGS. 1A-1B includes an actuator 20, a positioner 40 coupled with the actuator 20, and an implant interface 80 at the distal end of the positioner 40. A portion of the implant interface 80 may engage a complementary portion of an implant 100 in order to control the delivery (i.e., securing and detaching) of the implant 100 at the desired location. While the implant is shown or described in several embodiments as comprising an embolic coil 90, any implant (e.g., stents, filters, dilation balloons, thrombectomy devices, atherectomy devices, flow restoration devices, embolic coils, embolic protection devices, etc.) that is compatible with the subject technology may be used in accordance with the embodiments described herein.

FIG. 2A shows the positioning system 10 of FIGS. 1A-1B used inside a patient's vasculature. In the embodiment shown in FIG. 2A, an operator uses a guide tube or guide catheter 12 to position a delivery tube or microcatheter 14 in a patient's vasculature. This procedure involves inserting the guide catheter 12 into the patient's vasculature through an access point such as the groin, and directing the distal end 12a of the guide catheter 12 through the vascular system until it reaches the carotid artery. After removing a guide wire (not shown) from the guide catheter 12, a microcatheter 14 may be inserted into the guide catheter 12 and the distal end 14a of the microcatheter 14 subsequently exits the guide catheter distal end 12a and may be positioned near the target site 16, such as an aneurysm in the patient's brain.

Figure 2B:
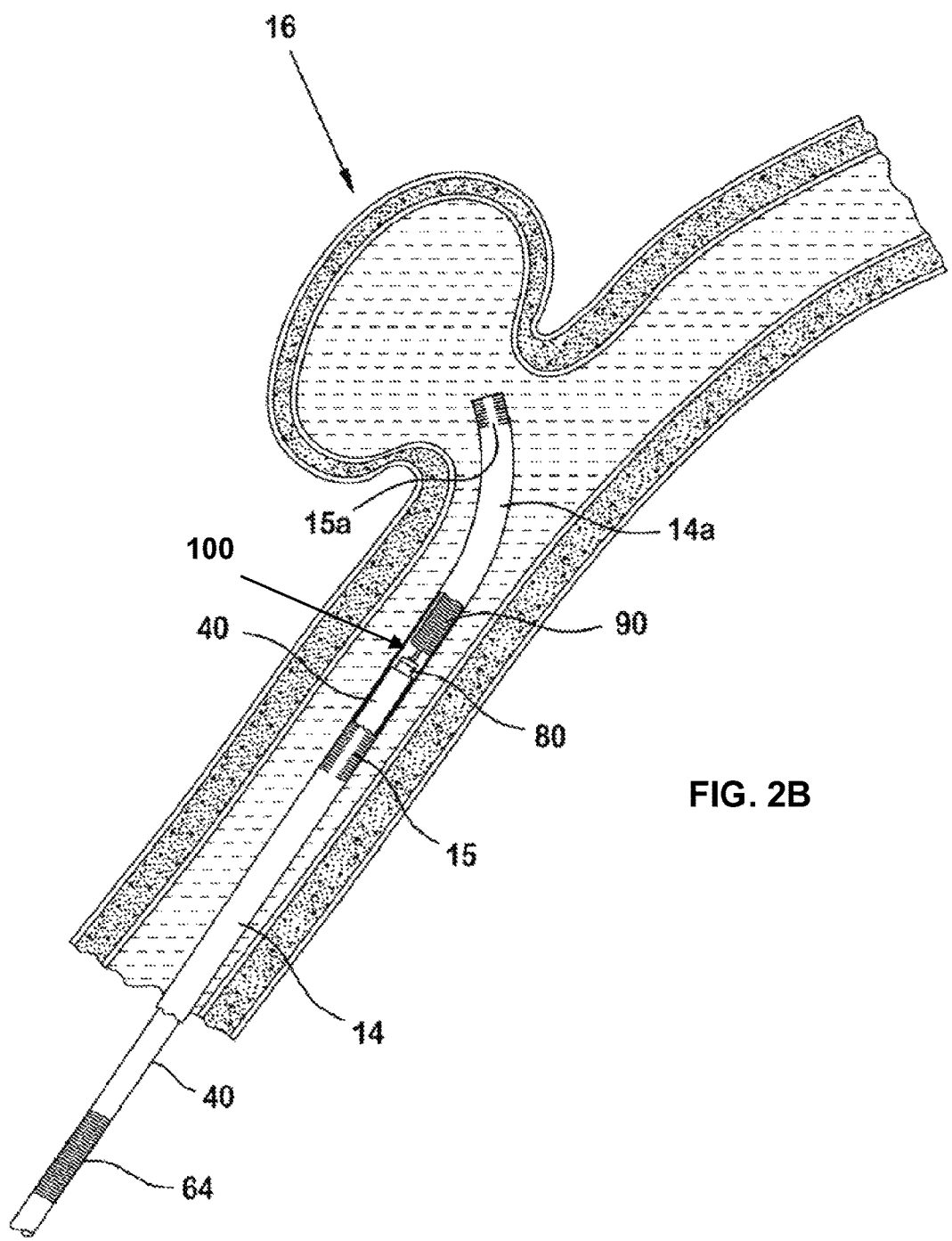
FIG. 2B shows a closer view of a portion of FIG. 2A showing the positioning system in partial cross-section and an exemplary implant in accordance with some embodiments of the subject technology in a position within the human body.
Figure 2C:
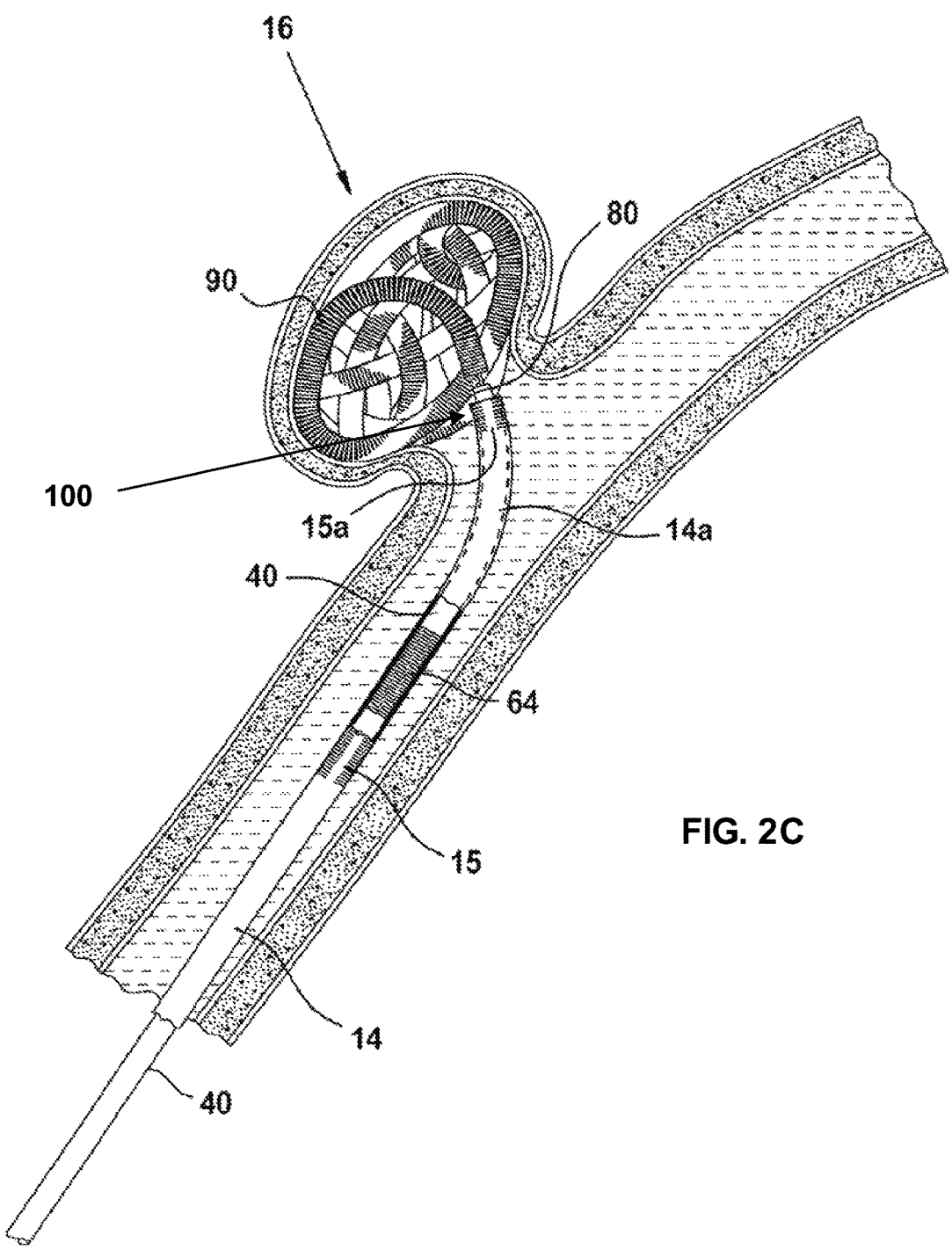
FIG. 2C shows a closer view of a portion of FIG. 2A showing the positioning system in partial cross-section and an exemplary implant in accordance with some embodiments of the subject technology in another position within the human body.

In the embodiments illustrated in FIGS. 2B and 2C, the microcatheter 14 also includes microcatheter markers 15 and 15a that facilitate imaging of the distal end 14a of the microcatheter 14 with common imaging systems. After the distal end 14a reaches the target site 16, the positioning system 10 of the illustrated embodiment is then inserted into the microcatheter 14 to position the implant interface 80 at the distal end of the positioner 40 near the target site 16, as illustrated in FIG. 2C. The implant 100 can be attached to the implant interface 80 prior to inserting the positioning system 10 into the microcatheter 14. This mode of implant delivery is illustrated in FIGS. 2A-2C. The delivery of the implant 100 is facilitated by disposing the microcatheter marker 15a near the target site 16, and aligning the microcatheter marker 15 with a positioner marker 64 in the positioner 40 which, when the two markers (markers 15 and 64) are aligned with each other as illustrated in FIG. 2C, indicates to the operator that the implant interface 80 is in the proper position for the release of the implant 100 from the positioning system 10.

Referring to FIGS. 1A-1B, the implant interface 80 is a portion of the positioning system 10 that allows the operator to mechanically control the engagement and disengagement of the implant 100 to the positioner 40, and allows the positioner 40 to retain the implant 100 in a way that minimally contacts the implant 100, that permits movement of the implant relative to the positioner in some or all of axial, tilt, and rotational directions, and that in some embodiments allows the implant 100 to move axially and without radial movement when engaging and disengaging the implant interface 80.

Figure 3:
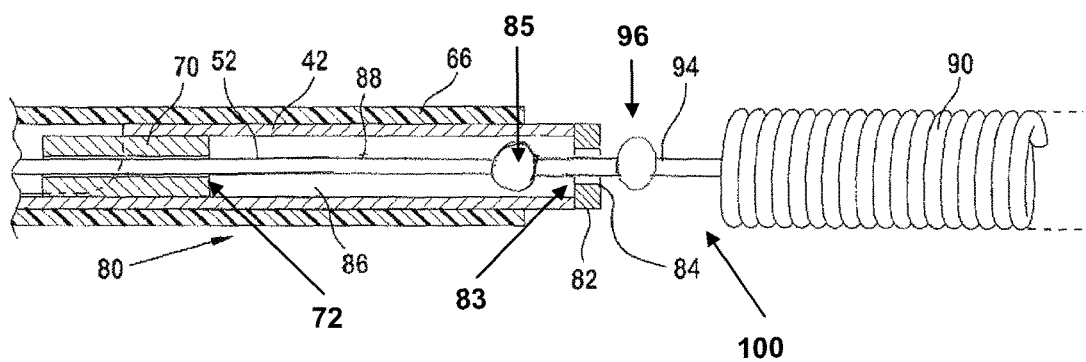
FIG. 3 shows a closer view of a portion of an exemplary implant interface in accordance with some embodiments of the subject technology.
Figure 4:
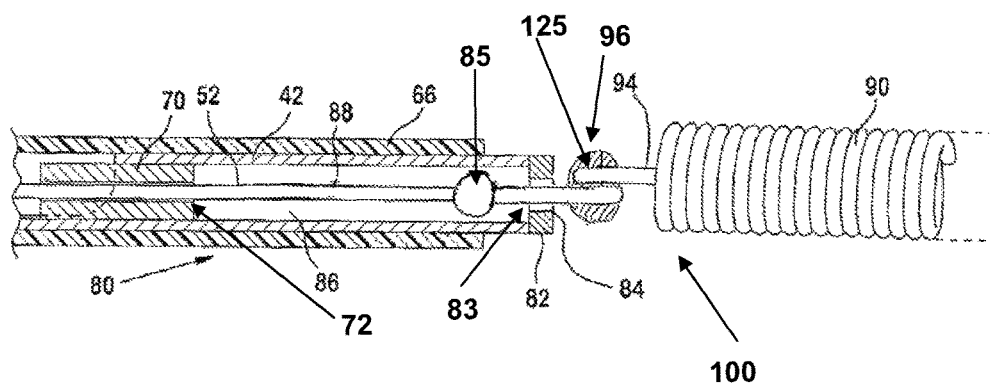
FIG. 4 shows a closer view of a portion of an exemplary implant interface in accordance with some embodiments of the subject technology.

The implant interface 80 provides mechanical control of the engagement and disengagement of the implant 100 by retaining a member engaging the implant 100. In some embodiments, this member is a securing member 94 that is coupled at its proximal end to the distal tip 88 of an elongate member 52 such as shown in FIGS. 3-4. The securing member 94 is also coupled to a structure such as embolic coil 90 at its distal portion. In the embodiment shown in FIGS. 3-4, the elongate member 52 is disposed in the cavity 86 that is defined by the distal surface 72 of the stopper 70, the proximal surface 83 of the end cap 82, and the inner walls of the positioner tube 42. A positioner tube sleeve 66 encloses the positioner tube 42 to provide a sliding exterior surface to the positioner tube 42 that facilitates the insertion and sliding of the positioner tube 42 into and through the microcatheter 14 (FIGS. 2A-2C). The distal end of the cavity 86 terminates at an end cap 82 which has a port 84 for communicating with the distal exterior environment. The implant interface 80 may also include an enlarged portion 96 and a stop element 85.

An implant may be any implant that can be retained and positioned by a positioning system (e.g., a catheter delivery system). Suitable examples of implants include, but are not limited to, stents, filters, dilation balloons, thrombectomy devices, atherectomy devices, flow restoration devices, embolic coils, embolic protection devices, etc.

Referring to the embodiments shown in FIGS. 3-4, the implant 100 is depicted with the coil 90 being retained by the implant interface 80 by an extension (e.g., securing member 94) that engages or is coupled to the coil 90. The extension can be a part of the implant 100 when the implant 100 is made, a modified portion of the manufactured implant 100, or attached to the implant 100 after initial manufacturing.

In the embodiments illustrated in FIGS. 1A-1B, 2B-9A, 10-13A, and 14, the implant 100 is depicted as comprising an embolic coil 90. FIGS. 1A-1B shows the coil 90 in a coiled orientation prior to insertion into the microcatheter 14. For simplicity, the implant 100 shown in FIGS. 2B-9A, 10-13A, and 14 is in a truncated form and disposed in alignment with the axis and the interior of the microcatheter (not shown). The implant 100 shown in FIG. 2C is shown in an implanted state, disposed in an aneurysm.

Referring to FIG. 14, the implant 100 may comprise (i) a coil 90 having a proximal portion and a distal portion; (ii) a stretch-resistant member 112 extending through the coil 90 and having a proximal end and a distal end, the stretch-resistant member 112 distal end coupled to the coil 90 distal portion; (iii) a reduced dimension proximal portion which may be a crimped portion 116 of a coil shell 118 disposed at the proximal end of the stretch-resistant member 112, and which can be otherwise free of the proximal portion of the coil 90. In some embodiments, the crimped portion 116 may be welded to the proximal portion of the coil 90.

In particular, the crimped portion 116, with a reduced dimension, and the coil 90 may be free to rotate around the central axis of the implant 100 as facilitated by the illustrated embodiments. As shown in FIG. 14, the distal portion of the stretch-resistant member 112 extends through the coil lumen 105 defined by the coil 90 and is coupled to coil 90 at the distal end (e.g., by a polymer melt 114), which allows the coil 90 have free rotation about a longitudinal axis. In some existing systems, the implant or a portion of the implant may be firmly held by the delivery system and is not free to rotate and, when the implant and delivery system are advanced distally to the target site through a microcatheter, the surface of the implant (especially the helical surface of some coils) can induce a torque within the implant when moved along the lumen of a microcatheter. That torque is stored as a potential energy in a compressed spring within the implant itself and within the connection between the implant and the delivery system. When the implant 100 then emerges from the microcatheter 14 at the target site, it is believed that the potential energy can be released suddenly and cause the implant to twist unpredictably and deposit itself in an undesirable location.

The positioning system 10 facilitates the unhindered rotation of the crimped portion 116 and coil 90, thereby avoiding this problem that exists with some delivery systems. The free rotation of the coil 90 and crimped portion 116 allows the implant 100 to be deployed from the microcatheter 14 at the target site 16 much more gently than with some systems having a connection that is rigid or that partly or wholly limits movement and rotation between the implant and delivery system, and the free rotation also lowers the force applied to the vasculature during deployment and positioning of the implant 100 at the target site 16.

Commercially available embolic coils suitable for use with the positioning system 10 include the Sapphire™, Axium™, NXT™, and Nexus™ embolic coils, commercially available from EV3, Inc. of Plymouth, Minn. USA. Although the implant 100 of the illustrated embodiment comprises an embolic coil, the implant 100 may be any implant that can be inserted with a catheter, such as a stent, a filter, a dilation balloon, a thrombectomy device, an atherectomy device, a flow restoration device, an embolic coil, or an embolic protection device.

Commercially available stents suitable for use with the delivery system 10 include the IntraStent®, ParaMount™, PRIMUS™, PROTÉGÉ®, and Solitaire™ stents, commercially available from EV3, Inc. of Plymouth, Minn. USA.

A commercially available embolic protection device suitable for use with the delivery system 10 is the SpideRX® embolic protection device, commercially available from EV3, Inc. of Plymouth, Minn. USA.

While aspects of an exemplary positioner are described herein, any positioner that is compatible with the subject technology may be used in conjunction with this disclosure. The positioner 40 provides the operator the ability to move the implant 100 controllably through the microcatheter 14 and to position the implant properly at the target site 16. The positioner 40 provides a mechanical system for selectively engaging the implant 100, while maintaining a narrow profile and sufficient flexibility to navigate the tortuous pathways within the body to reach the target site 16. While providing a small and flexible profile, the positioner 40 has sufficient strength to allow the operator to controllably move the implant 100 through the microcatheter 14, and the mechanical engagement with the implant 100 remains functional and controllable when subjected to high tortuosity near the target site 16.

The mechanical engagement of the positioner 40 to the implant 100 also maintains the proper orientation of the implant 100 throughout the positioning procedure by allowing the implant 100 to rotate and discharge any torsional forces induced during the movement of the implant 100 to the target site 16. The positioner 40 also allows the operator to control the movement of the positioner 40 and implant 100 by properly translating the control exerted by the operator into predictable and responsive movements near the target site 16.

While aspects of an exemplary actuator and actuator interface are described herein, any actuator and/or actuator interface that is compatible with the subject technology may be used in conjunction with this disclosure. The actuator interface 80 provides the operator the ability to control the movement of the implant 100 as it is positioned by the positioning system 10, and to mechanically control the selective engagement and disengagement of the implant 100 and implant interface 80. The actuator interface 80 controls the movement of the implant 100 by providing a surface upon which the operator can exert control, so that the controlling motions of the operator are accurately transferred to the implant interface 80 and implant 100 through the positioner 40.

The actuator 20 provides a mechanism that removably engages the actuator interface 80 and causes the controllable and predictable movement of the actuator interface 80. The actuator 20 also provides a design that allows the operator to hold the actuator 20 firmly in place, in order to maintain the position of the positioner 40 relative to the target site 16, and allows the operator to utilize the actuator 20 in a controlled manner that minimizes the movement of the positioner 40.

The proximal portion (e.g., enlarged portion 96, etc.) of the implant 100 is generally designed to be complementary to the distal portion (e.g., end cap 82, port 84, etc.) of the tubular member (e.g., positioner tube 42, catheter, etc.). Prior to the delivery of the implant 100 to the target site 16, the implant 100 may be coupled, either directly or indirectly, to the implant interface 80. FIGS. 3-14 show closer views of various exemplary embodiments of the implant interface 80 and mechanisms for detaching the implant 100 from the implant interface 80. While the various exemplary embodiments include the delivery of coil implants, any compatible implants may be used in accordance with the embodiments described herein.

FIGS. 3-14 show various exemplary assemblies for deploying an implant 100 in a vasculature. In some embodiments, the assembly may include a tubular member (e.g., position tube 42) defining a member lumen (e.g., cavity 86) within the tubular member and further defining an opening (e.g., port 84) at the distal portion (e.g., end cap 82) of the tubular member. One or more of the assemblies may further include an implant 100 extending distally from the positioner tube 42 and an elongate member 52 moveably disposed within the positioner tube 42.

In some embodiments, the implant 100 is configured for placement into an aneurysm or other treatment site within a patient. In some embodiments, the implant 100 may include an embolic coil 90 formed by a wire, filament, or other elongate member helically-wrapped about a central axis to form a generally tubular structure. As shown in FIG. 14, the coil 90 may define a lumen 105 therein which extends axially along the length of the coil 90. The implant 100 may further include an enlarged portion 96 coupled to or otherwise forming an integral part of the securing member 94, which extends into the lumen 105 and is coupled to or otherwise forms an integral part of the implant 100 (e.g., coil 90). The coil 90 may be coupled to the distal region of the securing member 94, which extends through the coil lumen 105. In some embodiments, the enlarged portion 96 may be positioned within the cavity 86 proximal to the opening (e.g., port 84). In certain embodiments, however, the enlarged portion 96 may be positioned outside the cavity 86, as illustrated, distal to the opening. In some embodiments, the enlarged portion 96 may be larger than the opening. In some embodiments, the enlarged portion 96 may be smaller than the opening.

Figure 12:
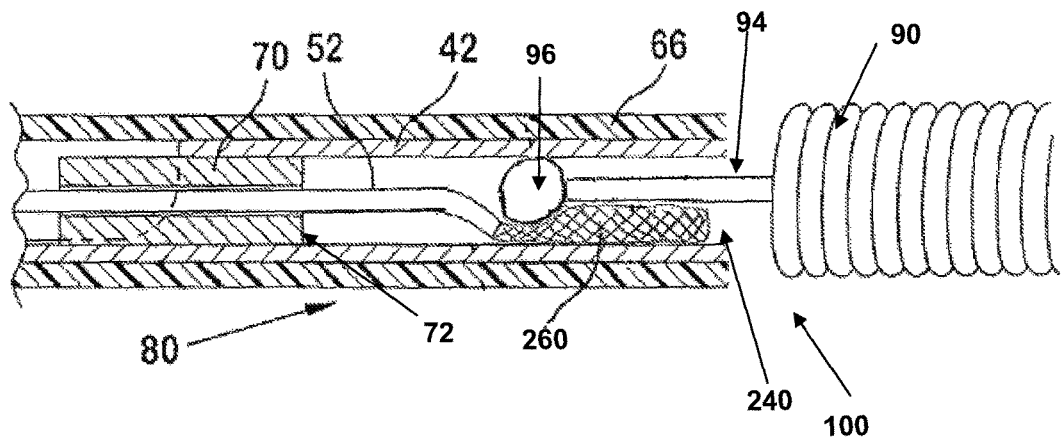
FIG. 12 shows a closer view of a portion of an exemplary implant interface in accordance with some embodiments of the subject technology.

In some embodiments, the elongate member 52 extends within the tubular member lumen. In some embodiments, the elongate member 52 extends distally through the port 84. In some embodiments, the elongate member 52 may be coupled to the enlarged portion 96. In some embodiments, the elongate member 52 has a distal segment 88 that extends past the enlarged portion 96. In some embodiments, the elongate member 52 contacts the distal-facing surface 130 (FIG. 7-10) of the enlarged portion 96 thereby retaining the enlarged portion 96. In some embodiments, the elongate member 52 has an expandable body 140 (FIG. 12). In some embodiments, the expandable body 140 may be expanded distally to the enlarged portion 96 thereby retaining the enlarged portion 96. In some embodiments, the elongate member 52 is positioned at least partially distal to the enlarged portion 96.

FIGS. 3-5, 7-10, 12, and 14 relate to embodiments that detach or release the implant 100 through a proximal motion of the elongate member 52. This proximal motion may be achieved by, for example, pulling proximally on the elongate member 52 with respect to the tubular member or pushing on the tubular member such that the tubular member moves distally with respect to the elongate member 52 or both.

Figure 6:
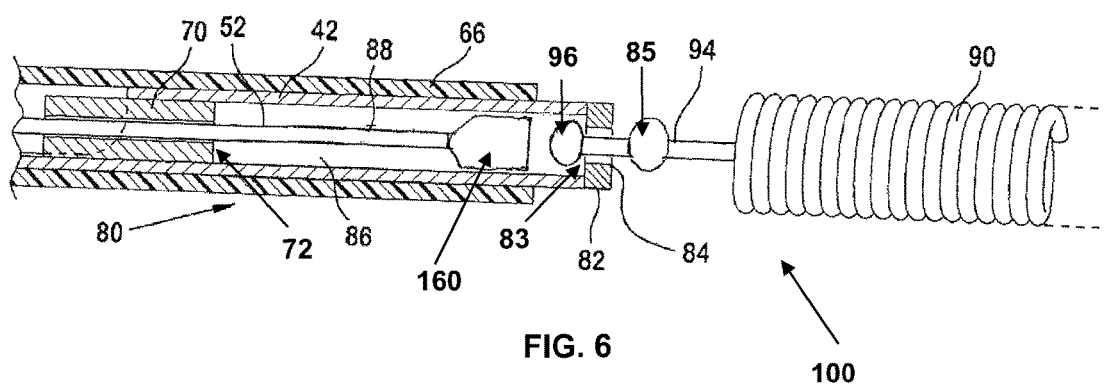
FIG. 6 shows a closer view of a portion of an exemplary implant interface in accordance with some embodiments of the subject technology.
Figure 11:
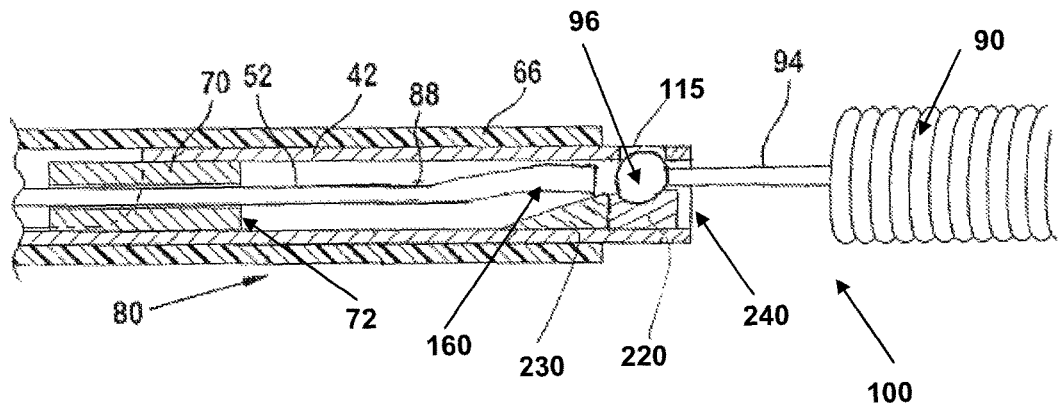
FIG. 11 shows a closer view of a portion of an exemplary implant interface in accordance with some embodiments of the subject technology.

FIGS. 6 and 11 relate to embodiments that detach or release the implant 100 by a distal translation of the elongate member 52. This distal translation may be achieved by, for example, pushing the distal portion 88 of the elongate member 52 such that elongate member 52 moves distally with respect to the tubular member or pulling on the tubular member such that the tubular member moves proximally with respect to the elongate member 52 or both.

In the embodiments shown in FIGS. 3-4, the implant interface 80 includes a cavity 86 defined at least in part by a tubular member, a positioner tube 42, an end cap 82, a stopper 70, an elongate member 52 and its distal portion 88, a positioner tube sleeve 66, and a stop element 85.

In particular, the positioner tube 42, the end cap 82, and the distal facing wall 72 of the stopper 70 define a cavity 86 within the implant interface 80. The stopper 70 can function to guide and control the movement of the distal portion 88 of the elongate member 52.

In some embodiments, the positioner tube 42 is made from a material that is flexible and strong enough to transfer forces applied by the operator (e.g., a surgeon) at the proximal end to the implant interface 80. Suitable examples of materials include, but are not limited to, 304 stainless steel hypotube, polymeric extrusion, braided extrusion, or engineering polymer materials (e.g., polyether ether ketones (PEEK), polyimide, nylon, polyester, etc.) that can have about 0.010 to about 0.018 inch outer diameter and about 0.005 to about 0.012 inch inner diameter, with about 10 to about 60 cm length of the distal end of the positioner tube 42 ground to about 0.008 to about 0.016 inch outer diameter to reduce girth and increase flexibility. The positioner tube 42 may be comprised of slots, holes, laser cuts, or other structures to provide flexibility to portions of or all of the positioner tube 42. As will be appreciated, the dimensions and/or materials of the positioner tube 42 may vary without departing from the scope of the disclosure.

In some embodiments, the end cap 82 is made of about 0.001 to about 0.005 inch thick 304 stainless steel, a polymeric material, or a steel alloy retainer ring with about 0.008 to about 0.018 inch outer diameter and about 0.003 to about 0.009 inch diameter port welded or bonded to the distal end of the positioner tube 42. As will be appreciated, the dimensions and/or materials of the end cap 82 may vary without departing from the scope of the disclosure.

In some embodiments, the stopper 70 is made of 304 stainless steel, a platinum alloy, a polymeric extrusion, a braided extrusion, or a non-elongating polymeric material with about 0.001 to about 0.012 inch inner diameter, and is coupled (e.g., welded or glued) to the interior of the positioner tube 42. The dimensions and/or materials of the stopper 70 may also vary, without departing from the scope of the disclosure.

In some embodiments, the elongate member 52 is a cord, a wire, a rod, a tubular, a thread or a filament made of a metal or a polymer. The cross-section of the elongate member 52 may be circular. In certain embodiments, however, the cross-section may be other shapes, such as polygonal, without departing from the scope of the disclosure. In some embodiments, the elongate member 52 has an outer diameter from about 0.001 to about 0.005 inch, but the outer diameter may vary, depending on the application.

As shown in FIGS. 3-4, the positioner tube sleeve 66 may encase or generally surround the longitudinal length of the positioner tube 42, thereby providing a sliding engagement between the positioner tube 42 and the positioner tube sleeve 66. The sliding engagement may facilitate the insertion and sliding of the positioner tube 42 into and through the microcatheter 14 (FIGS. 2A-2C). In operation, the positioner tube sleeve 66 may be configured to increase the lubricity between the positioner tube 42 and the inner lumen surface of the microcatheter 14 and to further increase the structural integrity of the positioner tube 42. As can be appreciated, it is particularly advantageous to reduce friction between the positioner tube 42 and the microcatheter 14 at the distal one third of the positioning system 10 as this distal-most portion is subject to tortuous anatomy that causes additional friction between moving components.

Figure 5:
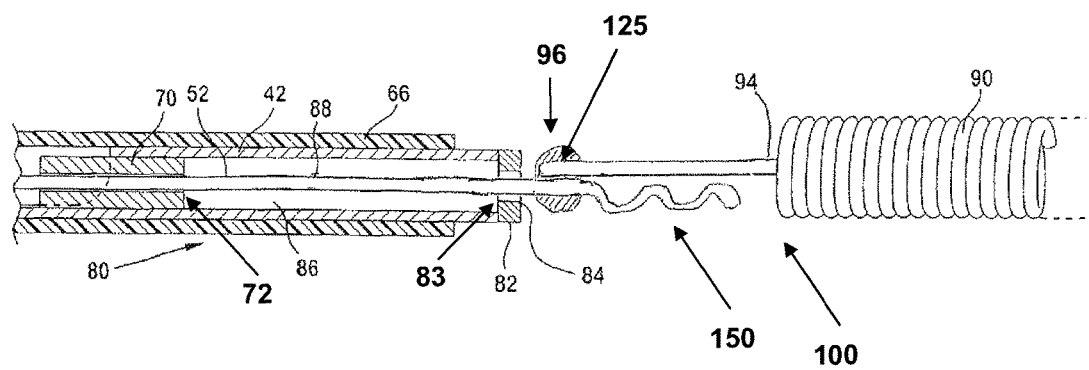
FIG. 5 shows a closer view of a portion of an exemplary implant interface in accordance with some embodiments of the subject technology.

As illustrated in FIGS. 3-5, the enlarged portion 96 may be coupled to the proximal end of the securing member 94, which is attached to the coil 90 at the proximal end of the coil 90 and positioned distal to the port 84. In the embodiments shown in FIGS. 3-5, the enlarged portion 96 has a cross-sectional area that is greater than a cross-sectional area of the port 84, which prevents the enlarged portion 96 from passing therethrough, and thereby prevents the coil 90 from coming into contact with the end cap 82. A stop member 85 may also be disposed within the cavity 86 and coupled to or otherwise formed integrally with the elongate member 52. The stop element 85 also has a cross-sectional area that is greater than the cross-sectional area of the port 84. Thus, the stop member 85 and the enlarged portion 96 limit the range of axial motion possible for the implant 100 to traverse while engaged at the implant interface 80, which in turn may be advantageous for greater accuracy and faster positioning of the implant 100 in the target site 16 (FIG. 2A). In these embodiments, the implant interface 80 and the implant 100 may be directly coupled to the elongate member 52 so that any longitudinal translation of the elongate member 52 corresponds to a similar or same translation of the securing member 94.

The implant 100 shown in FIG. 3 may be detached from the positioning system 10 according to at least the following embodiments. According to one or more embodiments, a proximal motion of the elongate member 52 can cause the enlarged portion 96 to come in contact with the end cap 82. This proximal motion can be achieved by any number of ways including pulling of the elongate member 52 away from the target site or pushing of the positioner tube 42 towards the target site or a combination of both. In some embodiments, the proximal motion is caused by an actuator positioned at the proximal portion of the positioning system 10. A longitudinal force applied proximally along the axis of the elongate member 52 can contribute to the release or the detachment of the implant 100. Given sufficient force, the securing member 94 can break so as to detachably release the implant 100 from the positioning system 10. In some embodiments, given sufficient force, at least one of the enlarged portion 96, securing member 94, and the elongate member 52 can break so as to detachably release the implant 100.

It is generally desirable to controllably break at least one of the securing member 94 and the elongate member 52 so that the break is localized to a relatively small portion along the securing member 94 or the elongate member 52. In some embodiments, the breakage occurs at a structurally weak spot such as, but not limited to, an etched, crimped, reduced diameter, annealed, or notched spot. In some embodiments, at least one of the securing member 94 and the elongate member 52 is made from a frangible material so that it tends to break up into, for example, two pieces rather than deforming plastically and retaining its cohesion as a single object. Examples of suitable frangible materials include, but not limited to, aluminum oxide, silicon dioxide, magnesium oxide, zirconia, cordierite, silicon carbide and the like. In some embodiments, the proximal portion of the elongate member and/or securing member 94 is frangible so that any breaking is localized to those portions. In some embodiments, at least one of the securing member 94 and the elongate member 52 may be configured to break inside the enlarged portion 96. In some embodiments, the distal portion 88 of elongate member 52 may break to release the implant 100. In some embodiments, the enlarged portion 96 may break to release the implant 100. In some embodiments, the stop element 85 may break to release the implant 100.

In some embodiments, the surfaces at or near the proximal portion of the securing member 94 and/or inner walls defined by a recess 125 of the enlarged portion 96 may have a topography that enhances frictional contact. The recess 125 is generally designed to receive and frictionally engage the securing member 94 through contact. In some embodiments, the securing member 94 and inner walls of the enlarged portion 96 may have periodic gratings that provide frictional contact with each other. In some embodiments, the inner walls of the enlarged portion 96 and/or the distal portion of the securing member 94 may be made from a material that has a relatively high frictional coefficient or have surfaces that are coarse. Examples of suitable materials include, but are not limited to, silicone rubber, acrylic rubber coatings, steel, cast iron, zinc, platinum, tungsten, etc. In some embodiments securing member 94, elongate member 52, or both may be secured to the enlarged portion 96 by compressing the enlarged portion 96 onto the securing member 94 and the elongate member 52. This may be accomplished by swaging, crimping, pressing, casting the enlarged portion 96 onto the securing member 94 and elongate member 52, by adhering enlarged portion 96 onto the securing member 94 and elongate member 52, or by other means.

In the embodiment shown in FIG. 4, the elongate member 52 extends distally through the port 84 and terminates outside the port 84. The securing member 94 is coupled to the distal portion 88 of the elongate member 52 through frictional contact with the enlarged portion 96. As shown in FIG. 4, the proximal end of the securing member 94 is disposed in the enlarged portion 96 and making frictional contact with inner walls of the recess 125 within the enlarged portion 96.

In the embodiment shown, a proximal motion of the elongate member 52 will cause the enlarged portion 96 to come in contact with the end cap 82. In some embodiments, a proximal force will cause the distal portion 88 of the elongate member 52 to disengage from the enlarged portion 96. In some embodiments, the proximal force causes the distal portion 88 of the elongate member 52 to disengage from the stop element 85. Although less likely, in certain embodiments, when a force applied proximally on the enlarged portion 96 is greater than the frictional force between the securing member 94 and the enlarged portion 96, the securing member 94 will disengage from the enlarged portion 96 and thereby detach the implant 100 from the positioning system 10.

In the embodiment shown in FIG. 5, the proximal portion of the securing member 94 may be engaged with the enlarged portion 96 that is coupled to an elongate member 52 that is at least partially disposed within the cavity 86 and extends distally through the port 84. As shown in FIG. 5, an obstructed portion 150 of elongate member 52 extends distally past the enlarged portion 96. This curved profile of the obstructed portion 150 increases the detach force required for the release of the implant 100 as compared to a non-undulating profile. In some embodiments, the curved profile may be any shape that obstructs the release of the curved portion 150. Suitable shapes include, but are not limited to, crimped shape, S-shape, O-shape, and the like. In some embodiments, the curved profile may have multiple peaks or an undulating profile (e.g., sinusoidal shape, helical, etc.).

A proximal motion of the elongate member 52 may cause the enlarged portion 96 to engage the end cap 82. If the force applied proximally on the elongated member 52 is greater than the detach force, the crimped portion 150 of the elongated member 52 will at least partially straighten and release from the enlarged portion 96, thereby detaching the implant 100 from the positioning system 10. In some embodiments, the crimped portion 150 of the elongated member 52 will be released from the enlarged portion 96 by sliding through an aperture in the enlarged portion 96.

In the embodiment shown in FIG. 6, the proximal portion of the securing member 94 is coupled to the stop element 85 and the enlarged portion 96. As shown in FIG. 6, the enlarged portion 96 is disposed in the cavity 86 proximal to the port 84 while the stop element 85 is positioned distal to the port 84 and proximal to the coil 90. This embodiment also includes a pusher 160 that is part of the distal portion 88 of the elongate member 52. The enlarged portion 96 has a cross-section that is generally larger than the cross-section of the port 84 so that the enlarged portion 96 is prevented or hindered from passing through the port 84.

In some embodiments, the end cap 82 may be a retaining ring that is made from a radially expandable material. Generally, any radially expandable material that is compatible with one or more embodiments may be used. Suitable examples of expandable materials may include, but are not limited to, silicone, thermoplastic elastomers, rubbers, metals, nickel-titanium alloys, polymers (e.g., polytetrafluoroethylene (PTFE), polyethylene terephthalate (PET), polyether ether ketones (PEEK)), etc. The pusher 160 may generally be used to apply a longitudinal force that causes a distal motion of the enlarged portion 96. This longitudinal force can cause the enlarged portion 96 to come into contact with the radially expandable end cap 82. Given a sufficient force, the enlarged portion 96 can engage the end cap 82 to forcibly expand the end cap 82 and allow the enlarged portion 96 to pass through port 84.

In certain embodiments, the enlarged portion 96 may be made from a deformable material. Given a sufficient longitudinal force that acts distally, the enlarged portion 96 can deform while engaging the end cap 82 to allow the enlarged portion 96 to pass through. In general, any deformable material that is compatible with one or more embodiments may be used. Suitable examples of deformable materials may include, but are not limited to, silicone, thermoplastic elastomers, biopolymers, rubbers, metals, nickel titanium alloys, etc.

In the embodiments shown in FIGS. 7-10, the enlarged portion 96 is disposed in the positioner tube 42 and coupled to a distal segment 88 of the elongated member 52 that at least partially extends around the enlarged portion 96. In some embodiments, the coupling between the enlarged portion 96 and distal portion 88 of the elongate member 52 may be achieved through a ball and socket connection (FIG. 7-8), a ball and a curved wire connection (FIG. 9A-9B), a pivot and cam (FIG. 10), a hinge joint, a pivot joint, and the like.

Figure 7:
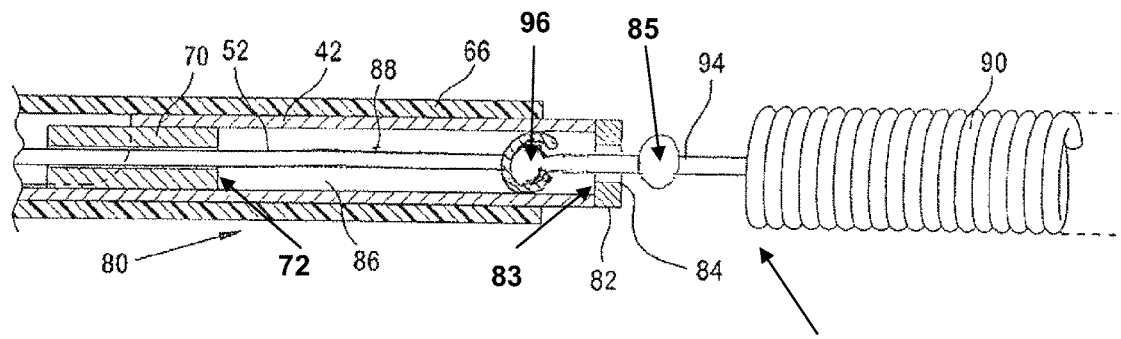
FIG. 7 shows a closer view of a portion of an exemplary implant interface in accordance with some embodiments of the subject technology.
Figure 8:
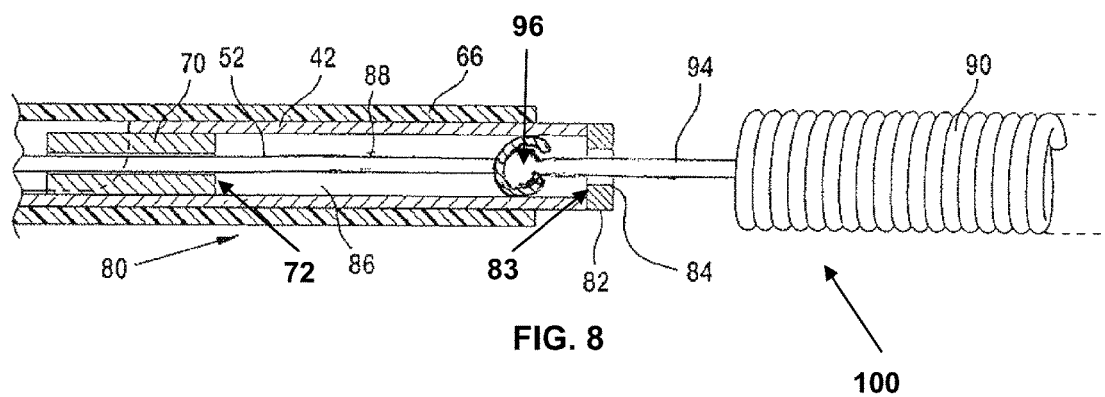
FIG. 8 shows a closer view of a portion of an exemplary implant interface in accordance with some embodiments of the subject technology.

In the embodiments shown in FIGS. 7-8, the enlarged portion 96, which can be a ball, is disposed in the positioner tube 42 while positioned proximal to the port 84 and coupled to the proximal portion of the securing member 94. In the embodiment shown in FIG. 7, a stop element 85 is positioned distal to the port 84 and proximal to the coil 90. While the enlarged portion 96 is generally small enough to fit or pass through port 84, the stop element 85 is generally large enough to abut the port 84 when drawn proximally. The socket element 170 is coupled to the distal portion 88 of the elongated member 52 and disposed in the positioner tube 42. As shown in FIGS. 7-8, the socket element 170 is configured to at least partially envelope or contact the distal facing surface 130 of the enlarged portion 96, which at least partially helps to retain the enlarged portion 96.

In some embodiments, the socket element 170 may further include at least one spring loaded element (e.g., a leaf) that promotes release of the enlarged portion 96 upon a proximal pulling motion on the socket element 170. In some embodiments, the proximal pulling motion may cause an elastic or plastic deformation of the socket element 170, which allows the release of the enlarged portion 96. The socket element 170 may generally be made from any material that is compatible with one or more embodiments. Suitable materials include, but are not limited to, alloys (e.g., nickel-titanium, titanium-palladium-nickel, Elgiloy, stainless steel, nickel-iron-zinc-aluminium, bronze, platinum alloys, titanium alloys, etc.), thermoplastics, metals (platinum, titanium, etc.), ceramics, etc. In some embodiments, the socket element 170 may include a partially spherical recess defined by the socket and a slot (not shown) that extends through a portion of the recess. In some embodiments, the enlarged portion 96 may be coupled to the socket element 170 by pivoting the elongated member 52, securing member 94, or both so that the securing member 94 may slide into the slot while the enlarged portion 96 is disposed inside the partially spherical recess. Once the enlarged portion 96 is secured inside the recess, the ball and socket connection may be straightened out so as to keep a narrow profile during insertion into a positioner tube 42.

In the embodiment shown in FIGS. 9A-9B, the enlarged portion 96 is disposed in the positioner tube 42 and coupled to a curved wire 180 positioned at a distal segment 88 of the elongated member 52. As shown in FIG. 9A, the distal end of the positioner tube includes an opening 240 that is larger than the enlarged portion 96. The curved wire 180 partially extends around distal facing surface 130 of the enlarged portion 96 to retain the enlarged portion 96 within the positioner tube 42. FIG. 9B shows an end view of the curved wire 180, which shows a slot 75 that runs transversely and is designed to receive a securing member 94. The curved wire 180 may generally be made from any material that is compatible with one or more embodiments. Suitable examples of materials include, but are not limited to, alloys (e.g., nickel-titanium, titanium-palladium-nickel, Elgiloy, stainless steel, nickel-iron-zinc-aluminium, bronze, platinum alloys, titanium alloys, etc.) and metals (platinum, titanium, etc.).

Referring to FIGS. 9A-9B, the ball element 96 may be coupled to the curved wire element 180 by pivoting the elongated member 52, securing member 94, or both so that the securing member 94 may slide into the slot 75 while the ball element 96 is disposed inside the concave curvature defined by the curved wire 180. Once the ball element 96 is secured inside the concave curvature, the ball 96 and curved wire 180 connection may be straightened out as to keep a narrow profile during insertion into a positioner tube 42. In some embodiments, the curved wire 180 may extend distal to the opening 240 while the securing member 94 is positioned in the slot 75 and the enlarged portion 96 is retained by the concave curvature of the curved wire 180. A proximal motion of the elongate member 52 would draw the retained assembly into the positioner tube 42.

In some embodiments, the implant 100 may be released by plastically or elastically deforming the curved wire 180. Such deformations may be achieved by pulling the elongate member 52 proximally with a sufficient force such that coil 90 abuts positioner tube 42, which allows the curved wire 180 to straighten as it is drawn proximally past the enlarged portion 96. Optionally, the elongate member 94 may include a stop (not shown) similar to a stop element 85, which is placed proximal to the coil 90 and distal to the opening 240. The stop may be larger in size than the opening 240 and is able to abut edges of the opening 240 when the curved wire 180 is drawn proximally.

In the embodiment shown in FIG. 10, the enlarged portion 96 is disposed in the positioner tube 42 and positioned proximal to the port 84. In some embodiments, the enlarged portion 96 may be small enough to fit through port 84 or port 84 may be substantially same diameter of lumen of positioner tube 42. In the embodiment shown in FIG. 10, the enlarged portion 96 is attached to the proximal portion of the securing member 94 and further coupled to a pivot 190 and cam 200 element that is part of the distal portion of the elongated member 52. The elongated member 52 and the cam 200 are coupled at the rotatable pivot 190. The cam element 200 may be hemi-spherical or otherwise designed to partially receive the enlarged portion 96 therein. The cam element 200 and the pivot 190 may generally be made from any material that is compatible with one or more embodiments described herein. Suitable materials include, but are not limited to, alloys (e.g., nickel-titanium, titanium-palladium-nickel, Elgiloy, stainless steel, nickel-iron-zinc-aluminium, bronze, platinum alloys, titanium alloys, etc.), thermoplastics, metals (platinum, titanium, etc.), ceramics, etc.

In the engaged configuration shown in FIG. 10, the cam 200 is positioned so that a portion of its concave surface is engaging the distal facing surface of the enlarged portion 96. This allows the cam to retain the enlarged portion 96 within the positioner tube 42 as needed. In some embodiments, the cam 200 may further include a slot (not shown) for receiving and retaining the securing member 94.

In the embodiment shown in FIG. 10, the port 84 is larger than the enlarged portion 96 so that the enlarged portion 96 is able to pass through the port 84 once the pivot cam releases the enlarged portion 96. In some embodiments, the enlarged portion 96 is released from the cam 200 by drawing the elongate member 52 proximally until coil 90 contacts the end cap 82. Further proximal movement of the elongate member 52 causes the cam 200 to rotate about pivot 190, thereby disengaging the concave surface of the cam 200 from the distal surface of the enlarged portion 96 and freeing the enlarged portion 96 to travel distally thru the cavity 86 and out of the port 84. In certain embodiments, the port 84 is made from an expandable material and is smaller than the enlarged portion 96, as described above with respect to FIG. 6, and the enlarged portion 96 passes through the smaller dimensioned port 84 by applying a force sufficient to expand the port 84.

In the embodiment shown in FIG. 11, the enlarged portion 96 extends through the opening 240 and is disposed in the positioner tube 42. In the embodiment shown, the opening 240 is larger than the enlarged portion 96. FIG. 11 shows a pre-detachment configuration in which the enlarged portion 96 is locked in place on one side by the edges of an aperture 115 (side window) defined in the wall of the positioner tube 42. An elastomeric padding 220 contacts the side of the enlarged portion 96 that is opposed to the aperture 115. The elastomeric padding 220 may generally be made from any material that is compatible with one or more embodiments. Suitable examples of materials include, but are not limited to, silicone, thermoplastic elastomers, rubbers, polymers (e.g., polytetrafluoroethylene (PTFE), polyethylene terephthalate (PET), polyether ether ketones (PEEK)), etc.

The distal portion of the elongated member 52 comprises pusher 160, which is configured to engage the enlarged portion 96 by distal movement of the elongated member 52. A ramp 230 may also be disposed inside the positioner tube 42 and acts to guide the pusher 160 to engage the enlarged portion 96 during the detachment of the implant 100. In some embodiments, the implant 100 may be detached by pushing the pusher 160 against the enlarged portion 96, thereby causing the enlarged portion 96 to move distally within the positioner tube 42, compressing the elastomeric padding 220, and forcing the enlarged portion 96 distally out of the side window 115 and further distally out of the opening 240.

In the embodiment shown in FIG. 12, the enlarged portion 96 extends through the opening 240 and is disposed in the positioner tube 42. In the embodiment shown, the opening 240 is larger than the enlarged portion 96. FIG. 12 shows a pre-detachment configuration in which the enlarged portion 96 is coupled to the distal portion (compressed mesh 260) of the elongated member 52. The compressed mesh may be an expandable/compressible material that deformably locks the enlarged portion 96 inside the positioner tube 42 and proximal to the opening 240. Suitable examples of materials include, but are not limited to, woven or knitted metal wires comprised of, for example, Nitinol, stainless steel, Elgiloy, platinum alloys, titanium alloys, or other metals. The woven or knitted materials may also be comprised of, for example, polymers such as polypropene, polyethylene, polyethylene terephthalate (PET), or other materials. Additionally, the mesh 260 can be a foam comprised of, for example, polymers such as silicone, polypropylene, polyethylene, nylon, etc. or an elastomeric solid comprised of silicone rubber, butyl rubber, polyurethane, or other materials. At least a portion of the enlarged portion 96 is in contact with a wall within the cavity 86, and at least a portion of compressed mesh is in contact with a wall within the cavity 86 and engages a distally facing surface of the enlarged portion 96.

In some embodiments, the implant 100 may be detached by pulling the elongate member 52 proximally, causing the compressed mesh 260 to move proximally in relation to the enlarged portion 96, and drawing the coil 90 against the opening 240. In some embodiments, the coil 90 is larger than the opening 240, limiting further proximal movement of the coil 90. In some embodiments, the more distal portions of the compressed mesh 260 become compressed as the compressed mesh 260 is drawn proximally past the enlarged portion 96. Once the compressed mesh 260 is entirely proximal to the enlarged portion 96, the enlarged portion 96 may move distally within the positioner tube 42 and out of the opening 240.

In the embodiment shown in FIG. 13A-13B, the implant 100 includes an enlarged portion 96 that may have fins or fin-like structures (e.g., struts) that extend radially and transversely out from the central axis of the securing member 94. The fins or fin-like structures may generally be made from any material that is compatible with one or more embodiments of the subject technology. Suitable examples of materials include, but are not limited to, alloys (e.g., nickel-titanium, titanium-palladium-nickel, bronze, Elgiloy, stainless steel, titanium alloys, platinum alloys, etc.), metals (platinum, titanium, etc.), ceramics, etc. The fins or fin-like structures can also be comprised of, for example, polymers such as polypropene, polyethylene, polyethylene terephthalate (PET), or other materials. Additionally, the fins can be a foam comprised of, for example, polymers such as silicone, polypropylene, polyethylene, and nylon or an elastomeric solid comprised of silicone rubber, butyl rubber, polyurethane, or other materials.

The cross-section of the enlarged portion 96 may have any shape such as, for example, a star (FIG. 13B). The distal portion 250 of the enlarged portion 96 may also have a distal curvature (e.g., convexity or a concavity, not shown). While not shown, this embodiment may interact with an implant interface 80 such as shown in FIGS. 3-12. The enlarged portion 96 may be disposed in the positioner tube 42 through a port 84 that is smaller than the enlarged portion.

In some embodiments, the cross-section of the port 84 of the end cap 82 can be non-circular or have a shape that is complementary to the enlarged portion 96 (e.g., FIG. 13B). In these embodiments having a complementary port 84 and enlarged portion 96, detachment of the implant 100 may generally be accomplished by rotating the enlarged portion 96 to fit through the similarly shaped port 84 as by a "lock and key" mechanism.

In the embodiment shown in FIG. 14, the distal portion of the elongate member 52 extends past the port 84 and is disposed inside the implant coil lumen 105 where it is coupled to the coil lumen extending portion 112 of the securing member via a straight release mechanism. In the embodiment shown, the distal portion of the elongate member 52 engages an eyelet 110, or a portion thereof, that forms the proximal portion of the securing member 112. The distal portion of the elongate member 52 preferably terminates proximal to the eyelet 110, the distal portion forming a straight member. The coil may be crimped about the straight member to frictionally retain the straight member inside the coil shell 116. In some embodiments, the coil is swaged or otherwise plastically deformed about the straight member. Further, as shown in FIG. 14, a portion of the coil shell that is just distal to the port 84 is crimped around the portion of the elongate member 52 that is just proximal to the eyelet and just distal to the port 84. The crimped portion of the coil shell is severed from the rest of the coil shell 118.

In some embodiments, the crimped portion of the coil shell 116 is welded to the rest of the coil shell 118. In certain embodiments, the eyelet 110 may be separate and distinct from the elongate member 52. In some cases, the elongate member 52 may be frictionally retained within lumen of crimped portion 116. Proximally drawing the elongate member 52 liberates the elongate member 52 from lumen of the crimped portion 116. In certain embodiments, the eyelet 110 is attached or coupled to the crimped portion 116 by, for example, welding, adhesives, friction, etc. Optionally, a stop element 85 may be added to the elongate member 52 proximal to the port 84.

In some embodiments, the elongate member 52 is coupled to the eyelet 110 by means of a line of weakness that separates when the elongate member 52 is pulled proximally, using means similar to those embodiments shown and/or described for FIG. 3.

While FIGS. 3-14 disclose specific embodiments, some or all of the features of the embodiments described herein may be used interchangeably or in combination with each other or with other embodiments.

In some embodiments, methods for deploying an implant 100 are provided. Suitable implants include, but are not limited to, stents, filters, dilation balloons, thrombectomy devices, atherectomy devices, flow restoration devices, embolic coils, embolic protection devices, or other devices, and the like. In some embodiments, the method includes: advancing in a vasculature, an assembly according to any of the embodiments described herein; and detaching the implant.

In some preferred embodiments, the assembly includes a tubular member (e.g., a catheter), a implant 100 configured for placement into an aneurysm, an enlarged portion 96, and an elongate member 52.

In some embodiments, the detachment of the implant 100 is achieved by withdrawing the elongate member 52 proximally relative to the tubular member, thereby separating the enlarged portion 96 from the elongate member 52 at the enlarged portion 96, to release the coil 90 at an aneurysm.

In some embodiments, the separating occurs at a location within the enlarged portion 96. In some embodiments, the separating includes breaking the elongate member 52. In some embodiments, the separating includes breaking the elongate member 52 within the enlarged portion. In some embodiments, the separating includes pulling the elongate member 52 from within the enlarged portion 96

In some embodiments, the separating occurs when a force applied to the elongate member 52 during the proximal movement exceeds a force maintaining a frictional coupling between the elongate member 52 and the enlarged portion 96. In some embodiments, the separating comprises withdrawing a distal segment of the elongate member through the enlarged portion, the segment having a curved profile. In some embodiments, the curved profile is a wave.

In some embodiments, the method includes: positioning in a vasculature, an assembly according to any of the embodiments described herein; and detaching the implant.

In some preferred embodiments, the assembly includes a tubular member, an implant 100, an enlarged portion 96 positioned in the member lumen proximal to the opening, and an elongate member 52.

In some embodiments, the detachment of the implant 100 is achieved by moving the elongate member 52 proximally relative to the tubular member to deform a distal segment of the elongate member 52, thereby releasing the enlarged portion 96 from the member lumen.

Referring to FIG. 3, the implant 100 may be detached from a tubular member (e.g., positioning system 10) by pulling proximally a longitudinal member (e.g., an elongate member 52) that includes an enlarged portion 96 positioned outside the tubular member and a stop element 85 positioned inside the tubular member, the longitudinal member being coupled to the implant 100. The longitudinal member is pulled proximally with a force sufficient to break the member to release the implant 100. In some embodiments, the implant 100 is detached by pushing the tubular member (e.g., positioning system 10 or positioner 10) distally. The tubular member's distal end preferably contacts an enlarged portion 96 (coupled to the implant 100), and the tubular member is pushed distally relative to the elongate member 52 with a force sufficient to break the member, thereby releasing the implant 100. The implant 100 may also include a stop element 85 (positioned inside the tubular member) that limits distal advancement of the longitudinal member as the stop element 85 contacts the end cap 82. In some embodiments, the stop element 85 on the longitudinal member absorbs forces (e.g., inadvertent longitudinal advancement or vibrations) that may be transferred to the implant 100 via the longitudinal member.

Referring to FIG. 4, the implant 100 may be detached from a tubular member (e.g., positioning system 10) by (i) coupling a longitudinal member that extends through a tubular member with an enlarged portion 96 that is frictionally coupled to an implant 100 and (ii) pulling the longitudinal member proximally with a force sufficient to overcome the frictional coupling. In some embodiments, the implant 100 is detached from a tubular member (e.g., positioning system 10) by pushing the tubular member relative to the longitudinal member or elongate member 52 with a force sufficient to overcome the frictional coupling.

Referring to FIG. 5, the implant 100 may be detached from a frictional coupling between a longitudinal member and an enlarged portion 96 of the implant 100 by pulling the longitudinal member proximally with a force sufficient to overcome the frictional coupling. In some embodiments, the implant 100 is detached from a tubular member (e.g., positioning system 10) by pushing the tubular member relative to the longitudinal member with a force sufficient to overcome the obstruction. Generally, a force sufficient to overcome the obstruction will conformationally change (e.g., straighten) the wavy or helical shape of the member extending distal to the enlarged portion 96. In some embodiments, the force is sufficient to conformationally change the shape of the member and overcome any frictional coupling between the longitudinal member and the enlarged portion 96.

Referring to FIG. 6, the implant 100 may be detached from the tubular member (e.g., positioning system 10) by using a pusher to apply a force distally on the enlarged portion 96 with a sufficient longitudinal force so that the enlarged portion 96 may be pushed through the expandable retaining ring (e.g., end cap 82). Generally, the sufficient longitudinal force will increase the cross-section of the port 84 to permit the enlarged portion 96 to pass therethrough.

Referring to FIG. 7-8, the implant 100 may be generally detached from a tubular member (e.g., positioning system 10) by withdrawing in a proximal direction the ball and socket connection once the implant 100 is ready to be deployed. The socket may be elastically or plastically deformed to allow the enlarged portion 96 to be withdrawn. Generally, the stop element or the coil will abut the distal end of the catheter to limit proximal withdrawal and further withdrawal to cause the socket to change shape, thus allowing the enlarged portion 96 to be released.

In those embodiments where the socket element 170 has a slot that helps to retain the implant 100, the ball and socket connection may be pivoted as to allow the free release of the implant 100. In some embodiments, the enlarged portion 96 may be smaller than the port 84. In some embodiments, the enlarged portion 96 may be larger than the port 84, which is expandable. In order to release the enlarged portion 96 from the smaller dimensioned port 84, a force sufficient to expand the port 84 as to allow the enlarged portion 96 to pass through is required.

Referring to FIGS. 9A-9B, the implant 100 may be detached from a tubular member (e.g., positioning system 10) by pivoting the ball and curved wire connection once the implant 100 is ready to be deployed. In the embodiment shown in FIG. 9A, the enlarged portion 96 has a cross-sectional size that is less than a cross-sectional area of the opening at the distal end of the tubular member. This allows the enlarged portion 96 to pass freely through the port 84 when the implant 100 is disengaged. In some embodiments, the enlarged portion 96 may be larger than the opening, which is made of an expandable material. In order to release the enlarged portion 96 from the smaller dimensioned port 84, a force sufficient to expand the port 84 may be applied to allow the enlarged portion 96 to pass through.

Referring to FIG. 10, the implant 100 may be detached from a tubular member (e.g., positioning system 10) by pulling proximally the elongated member 52 so that the cam 200 rotates about the pivot 190 to allow the enlarged portion 96 to release freely. In some embodiments, the cam 200 elastically or plastically deforms to release the enlarged portion 96.

Referring to FIG. 11, the implant 100 may be detached by applying a sufficient pushing force distally onto the enlarged portion 96 by the pusher 160 as to further deform elastomeric padding and allow the enlarged portion 96 to disengage from the aperture 115 and to advance past the opening 240.

Referring to FIG. 12, the implant 100 may be detached from a tubular member (e.g., positioning system 10) by pulling the elongated member 52 proximally so that the distal portion of the elongated member 52 slides against at least a portion of the enlarged portion 96. This sliding action causes the distal portions of the compressed mesh 140 to deform as to allow the enlarged portion 96 to be released and pass through the opening 240.

Referring to the implant 100 embodiments shown in FIGS. 13A-13B, these may be used in conjunction with a suitable implant interface 80 such as shown in, for example, FIG. 3. The implant 100 may generally be detached by applying a distal force sufficiently to the enlarged portion 96 (e.g. by a pusher shown in FIG. 6) such that the distal curvature 250 of the enlarged portion 96 may interact with end cap 82 and deform as to allow the enlarged portion 96 to pass through the port 84.

The enlarged portion 96 may have a non-circular cross-section. The port 84 may also have a non-circular cross-section that is complementary to the cross-section of the enlarged-portion 96. In such cases, the enlarged portion 96 can be rotated (or the tubular member is rotated) so that the enlarged portion 96 may fit through the port 84 to release the implant 100.

Referring to FIG. 14, the implant 100 may be detached by pulling the elongate member 52 proximally at a sufficient force to overcome the frictional resistance of the crimped connection thereby detaching the implant 100.

Referring to FIG. 14, methods for forming an attachment coupling of an implant assembly are provided. In one embodiment, the method includes plastically deforming a proximal portion of a coil implant onto an elongate member to create a friction coupling between the proximal portion and the elongate member. The proximal portion is positioned distal to an opening at a distal end portion of a tubular member through which the elongate member extends. In some cases, the deforming is achieved by crimping or swaging.

Referring again to FIG. 14, in another embodiment, the method includes forming a joint between a proximal portion of a coil implant and an elongate member such that a tensile strength of the joint is less than a tensile strength of the proximal portion and a tensile strength of the elongate member. The coupling proximal portion is preferably positioned distal to an opening at a distal end portion of a tubular member through which the elongate member extends. In some cases, the forming is achieved by welding or soldering.

The foregoing description is provided to enable a person skilled in the art to practice the various configurations described herein. While the subject technology has been particularly described with reference to the various figures and configurations, it should be understood that these are for illustration purposes only and should not be taken as limiting the scope of the subject technology.

There may be many other ways to implement the subject technology. Various functions and elements described herein may be partitioned differently from those shown without departing from the scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the scope of the subject technology.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

Terms such as "top," "bottom," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Furthermore, to the extent that the term "include," "have," or the like is used in the description or the claims, such term is intended to be inclusive in a manner similar to the term "comprise" as "comprise" is interpreted when employed as a transitional word in a claim.

The word "exemplary" is used herein to mean "serving as an example, instance, or illustration." Any embodiment described herein as "exemplary" is not necessarily to be construed as preferred or advantageous over other embodiments.

A reference to an element in the singular is not intended to mean "one and only one" unless specifically stated, but rather "one or more." The term "some" refers to one or more. Underlined and/or italicized headings and subheadings are used for convenience only, do not limit the subject technology, and are not referred to in connection with the interpretation of the description of the subject technology. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

While certain aspects and embodiments of the invention have been described, these have been presented by way of example only, and are not intended to limit the scope of the invention. Indeed, the novel methods and systems described herein may be embodied in a variety of other forms without departing from the spirit thereof. The accompanying claims and their equivalents are intended to cover such forms or modifications as would fall within the scope and spirit of the invention.

We claim:

1. A system for placing an implant at an aneurysm, comprising:
    a tubular member having (a) a member lumen in the tubular member and (b) an opening at a distal end portion of the tubular member;
    an implant configured for placement at an aneurysm and having an enlarged portion positioned in the member lumen proximal to the opening; and
    an elongate member extending in the lumen and having an expandable/compressible body (a) positioned at least partially distal to the enlarged portion in the lumen and (b) expanded distal to the enlarged portion to retain the enlarged portion in the lumen, and wherein the expandable/compressible body comprises a mesh.

2. The system of claim 1, wherein upon proximal movement of the elongate member relative to the tubular member, the body compresses and moves past the enlarged portion, thereby releasing the implant from the tubular member.

3. The system of claim 1, wherein the enlarged portion is substantially spherical.

4. The system of claim 1, wherein the opening at the distal end portion of the tubular member is larger than the enlarged portion.

5. The system of claim 1, wherein at least a portion of the enlarged portion is in contact with the tubular member, and at least a portion of expandable/compressible body is in contact with the tubular member and engages a distally facing surface of the enlarged portion.

6. A system for placing an implant at an aneurysm, comprising:
    a tubular member having a member lumen and an opening at a distal end portion of the tubular member;
    an implant having an enlarged portion positioned in the lumen proximal to the opening; and
    an elongate member extending in the lumen, the elongate member having an expandable/compressible body that contacts a distal-facing surface of the enlarged portion, thereby retaining the enlarged portion in the member lumen,
    wherein proximal movement of the elongate member relative to the end portion results in deformation of the expandable/compressible body to release the enlarged portion from the member lumen, and wherein the expandable/compressible body comprises a mesh.

7. The system of claim 6, wherein the enlarged portion is substantially spherical.

8. The system of claim 6, wherein the opening at the distal end portion of the tubular member is larger than the enlarged portion.

9. The system of claim 6, wherein at least a portion of the enlarged portion is in contact with the tubular member, and at least a portion of expandable/compressible body is in contact with the tubular member and engages the distal-facing surface of the enlarged portion.

10. A method for deploying an implant at an aneurysm, comprising:
    advancing in a patient's vasculature:
        (i) a tubular member comprising a member lumen and an opening at a distal end portion of the tubular member;
        (ii) an implant configured for placement at an aneurysm and having an enlarged portion positioned in the member lumen proximal to the opening;
        (iii) an elongate member extending in the lumen and having an expandable/compressible body (a) positioned at least partially distal to the enlarged portion in the lumen, and (b) expanded distal to the enlarged portion to retain the enlarged portion in the lumen, and wherein the expandable/compressible body comprises a mesh; and
    withdrawing the elongate member proximally relative to the tubular member to release the coil at the aneurysm.

11. The method of claim 10, wherein withdrawing the elongate member comprises withdrawing the elongate member until the expandable/compressible body is positioned proximal to the enlarged portion.

12. The method of claim 10, wherein withdrawing the elongate member comprises deforming the expandable/compressible body with the enlarged portion.

13. The method of claim 10, wherein withdrawing the elongate member comprises withdrawing the elongate member with a force that exceeds a force maintaining a frictional coupling between the expandable/compressible body and the enlarged portion.

14. The method of claim 10, wherein, after withdrawing the elongate member proximally relative to the tubular member, the enlarged portion of the coil passes through the opening at the distal end portion of the tubular member.

* * * * *

UNITED STATES PATENT AND TRADEMARK OFFICE
CERTIFICATE OF CORRECTION

PATENT NO. : 10,335,155 B2
APPLICATION NO. : 15/407361
DATED : July 2, 2019
INVENTOR(S) : Beckham et al.

Page 1 of 1

It is certified that error appears in the above-identified patent and that said Letters Patent is hereby corrected as shown below:

In the Claims

In Column 24, in Claim 10, Line 41, after "lumen" delete ",".

Signed and Sealed this
Twenty-seventh Day of August, 2019

Andrei Iancu
*Director of the United States Patent and Trademark Office*